United States Patent
Simson et al.

(10) Patent No.: US 11,593,931 B2
(45) Date of Patent: Feb. 28, 2023

(54) SURGICAL KIT INSPECTION SYSTEMS AND METHODS FOR INSPECTING SURGICAL KITS HAVING PARTS OF DIFFERENT TYPES

(71) Applicant: Howmedica Osteonics Corp., Mahwah, NJ (US)

(72) Inventors: Perry J. Simson, Bradenton, FL (US); Graeme A. Field, Jacksonville, FL (US); Patrick M. Caldwell, Jacksonville, FL (US)

(73) Assignee: Howmedica Osteonics Corp., Mahwah, NJ (US)

( * ) Notice: Subject to any disclaimer, the term of this patent is extended or adjusted under 35 U.S.C. 154(b) by 21 days.

(21) Appl. No.: 17/342,664

(22) Filed: Jun. 9, 2021

(65) Prior Publication Data

US 2021/0383523 A1 Dec. 9, 2021

Related U.S. Application Data

(60) Provisional application No. 63/036,596, filed on Jun. 9, 2020.

(51) Int. Cl.
*G06T 7/00* (2017.01)
*G06K 9/62* (2022.01)
(Continued)

(52) U.S. Cl.
CPC .............. *G06T 7/001* (2013.01); *A61B 34/70* (2016.02); *B25J 19/0066* (2013.01);
(Continued)

(58) Field of Classification Search
CPC ........... G06V 2201/034; G06V 30/153; G06V 20/10; A61B 2090/0805; A61B 34/70;
(Continued)

(56) References Cited

U.S. PATENT DOCUMENTS 5,515,599 A 5/1996 Best
7,164,968 B2 * 1/2007 Treat ..................... A61B 90/92
901/1
(Continued)

FOREIGN PATENT DOCUMENTS

DE 102010021037 A1 11/2011
JP 2022083768 A * 6/2022
(Continued)

OTHER PUBLICATIONS

Chen L, Zhang F, Zhan W, Gan M, Sun L. Optimization of virtual and real registration technology based on augmented reality in a surgical navigation system. Biomed Eng Online. Jan. 8, 2020;19(1):1. doi: 10.1186/s12938-019-0745-z. PMID: 31915014; PMCID: PMC6950982. (Year: 2020).*

(Continued)

*Primary Examiner* — Michael Robert Cammarata
(74) *Attorney, Agent, or Firm* — Howard & Howard Attorneys PLC

(57) ABSTRACT

Surgical kit inspection systems and methods are provided for inspecting surgical kits having parts of different types. The surgical kit inspection system comprises a vision unit including a first camera unit and a second camera unit to capture images of parts of a first type and a second type in each kit and to capture images of loose parts from each kit that are placed on a light surface. A robot supports the vision unit to move the first and second camera units relative to the parts in each surgical kit. One or more controllers obtain unique inspection instructions for each of the surgical kits to control inspection of each of the surgical kits and control movement of the robot and the vision unit accordingly to provide output indicating inspection results for each of the surgical kits.

20 Claims, 18 Drawing Sheets

(51) Int. Cl.
*A61B 34/00* (2016.01)
*G06T 7/60* (2017.01)
*G06V 20/10* (2022.01)
*G06T 7/73* (2017.01)
*B25J 19/00* (2006.01)
*G06V 30/148* (2022.01)

(52) U.S. Cl.
CPC .......... *G06K 9/6256* (2013.01); *G06T 7/0008* (2013.01); *G06T 7/60* (2013.01); *G06T 7/73* (2017.01); *G06V 20/10* (2022.01); *G06V 30/153* (2022.01); *G06T 2207/30164* (2013.01); *G06V 2201/034* (2022.01)

(58) Field of Classification Search
CPC ........ G06T 7/001; G06T 7/0008; G06T 7/60; G06T 2207/30164; G06K 9/6256
See application file for complete search history.

(56) References Cited

U.S. PATENT DOCUMENTS

| | | | |
|---|---|---|---|
| 7,180,014 B2 * | 2/2007 | Farber | G16H 40/20 606/1 |
| 7,557,710 B2 | 7/2009 | Sanchez et al. | |
| 7,644,016 B2 | 1/2010 | Nycz et al. | |
| 7,997,847 B2 | 8/2011 | Treat et al. | |
| 8,567,880 B2 | 10/2013 | Treat et al. | |
| 9,305,218 B2 | 4/2016 | Lewis et al. | |
| 10,071,856 B2 | 9/2018 | Hance et al. | |
| 10,154,885 B1 * | 12/2018 | Barnett | A61B 90/08 |
| 10,169,696 B2 | 1/2019 | Lee | |
| 10,239,701 B2 | 3/2019 | Wicks et al. | |
| 10,357,325 B2 | 7/2019 | Sayani et al. | |
| 10,360,531 B1 | 7/2019 | Stallman et al. | |
| 10,390,902 B2 | 8/2019 | Singh et al. | |
| 10,417,754 B2 | 9/2019 | Kimura et al. | |
| 10,504,623 B2 | 12/2019 | Woods et al. | |
| 10,517,680 B2 | 12/2019 | Moctezuma et al. | |
| 10,520,926 B2 | 12/2019 | Scelsi et al. | |
| 11,439,469 B2 * | 9/2022 | Poltaretskyi | A61B 90/361 |
| 11,443,501 B2 * | 9/2022 | Donhowe | A61B 34/37 |
| 2007/0268133 A1 * | 11/2007 | Sanchez | G08B 13/2462 340/568.1 |
| 2008/0108873 A1 * | 5/2008 | Gattani | H04N 5/23296 382/128 |
| 2009/0317002 A1 * | 12/2009 | Dein | A61B 90/90 340/568.1 |
| 2015/0224650 A1 * | 8/2015 | Xu | B25J 9/1692 414/730 |
| 2015/0324739 A1 | 11/2015 | Baker et al. | |
| 2016/0042130 A1 | 2/2016 | Broninx | |
| 2016/0074128 A1 | 3/2016 | Dein | |
| 2016/0328813 A1 | 11/2016 | Montgomery et al. | |
| 2017/0032313 A1 | 2/2017 | McCullough et al. | |
| 2017/0098049 A1 | 4/2017 | Sweeney | |
| 2017/0243157 A1 | 8/2017 | Piron et al. | |
| 2019/0080446 A1 * | 3/2019 | Kuzmin | G06V 10/44 |
| 2019/0142304 A1 | 5/2019 | Crawford et al. | |
| 2019/0261566 A1 | 8/2019 | Robertson et al. | |
| 2019/0279354 A1 | 9/2019 | Inazumi et al. | |
| 2019/0290796 A1 * | 9/2019 | Ma | G06V 10/945 |
| 2019/0303721 A1 | 10/2019 | Kurtz et al. | |
| 2019/0321126 A1 * | 10/2019 | Otto | G06T 7/74 |
| 2019/0389070 A1 | 12/2019 | Sirkett | |
| 2020/0005069 A1 | 1/2020 | Wang et al. | |
| 2020/0034591 A1 | 1/2020 | Bachelder et al. | |
| 2020/0184248 A1 * | 6/2020 | Donhowe | A61B 90/37 |
| 2020/0193241 A1 * | 6/2020 | Katayama | G06V 10/44 |
| 2020/0205926 A1 * | 7/2020 | Keibel | A61B 50/20 |
| 2020/0273581 A1 * | 8/2020 | Wolf | G06V 20/52 |
| 2020/0397509 A1 * | 12/2020 | Chen | G06V 10/82 |
| 2021/0193310 A1 * | 6/2021 | Jacobs | G06V 20/20 |
| 2021/0212784 A1 * | 7/2021 | Ramadorai | G06V 20/64 |
| 2021/0268659 A1 * | 9/2021 | Olmstead | G06V 10/751 |
| 2021/0344820 A1 * | 11/2021 | Boren | H04N 5/247 |
| 2022/0292815 A1 * | 9/2022 | Donnelly | G06V 10/774 |

FOREIGN PATENT DOCUMENTS

| | | | | |
|---|---|---|---|---|
| WO | 2005020063 A1 | | 3/2005 | |
| WO | WO-2008033574 A2 * | | 3/2008 | A61B 46/00 |
| WO | 2018228818 A1 | | 12/2018 | |
| WO | WO-2018221599 A1 * | | 12/2018 | A61B 34/20 |
| WO | WO-2019045282 A1 * | | 3/2019 | G01N 21/01 |
| WO | WO-2020031192 A1 * | | 2/2020 | F16M 11/08 |
| WO | 2021115583 A1 | | 6/2021 | |
| WO | WO-2021124716 A1 * | | 6/2021 | A61B 1/00009 |
| WO | WO-2021216535 A1 * | | 10/2021 | A61B 34/20 |

OTHER PUBLICATIONS

Advanced Illumination, "DL 194 General Purpose Diffuse Lights Specification Sheet", Dec. 14, 2016, Updated May 17, 2017, 4 pages.
Advanced Illumination, "DL 2230 Extra Small Dome Light Specification Sheet", Dec. 14, 2016, Updated May 17, 2020, 4 pages.
Cognex, "Deep Learning for Machine Vision—VisionPro Vidi 3.1 Video", https://www.cognex.com/resources/on-demand-webinars/deep-learning-for-machine-vision-visionpro-vidi-3-1 2021, 4 pages.
Cognex, "Deep Learning vs. Machine Vision", 2019, 12 pages.
Cognex, "ViDi Deep Learning for Factory Automation Best Practices Guide", 2019, 16 pages.
Cognex, "VisionPro ViDi Brochure", 2019, 2 pages.
Edmund Optics, "TechSpec Compact Fixed Focal Length Lens #59-870 16 mm FL f/1.6", 2014, 5 pages.
Edmund Optics, "TechSpec Compact Fixed Focal Length Lens #59-872 35 mm FL f/1.65", 2014, 5 pages.
English language abstract and machine-assisted English translation for DE 10 2010 021 037 A1 extracted from espacenet.com database on Jun. 16, 2021, 15 pages.
English language abstract for WO 2018/228818 A1 extracted from espacenet.com database on Jun. 16, 2021, 2 pages.
O'Mahony, Niall, "Deep Learning vs. Traditional Computer Vision", 2020, 17 pages.
Opto Engineering, "Product Data Sheet—ENMT-M1224-MPW2-MM", 2020, 2 pages.
Opto Engineering, "Product Data Sheet—MC150X", 2020, 3 pages.
Optotune, "Datasheet: EL-10-30-Series", 2019 16 pages.
Tabernik, Domen et al., "Segmentation-Based Deep-Learning Approach for Surface-Defect Detection" Jun. 11, 2019, 17 pages.
Universal Robots, "e-Series from Universal Robots Brochure", Jun. 2018, 12 pages.
Wilson, Andy, "Lens Choices Proliferate for Developers of Machine Vision Systems", Visions System Design, Sep. 12, 2016, 9 pages.

* cited by examiner

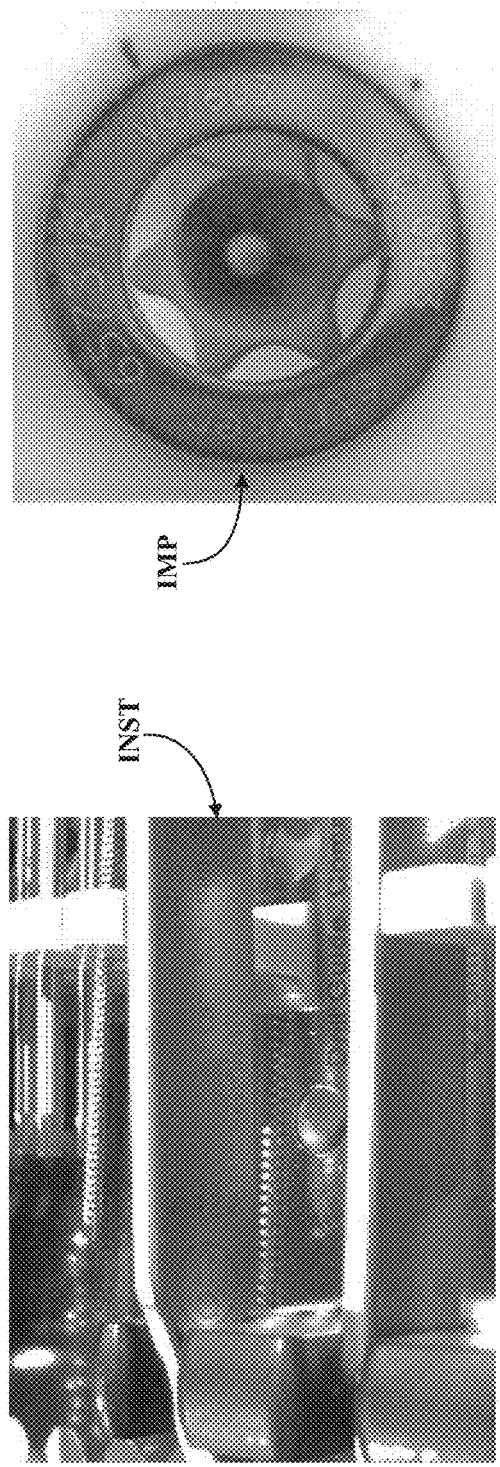
FIG. 7A
FIG. 7B
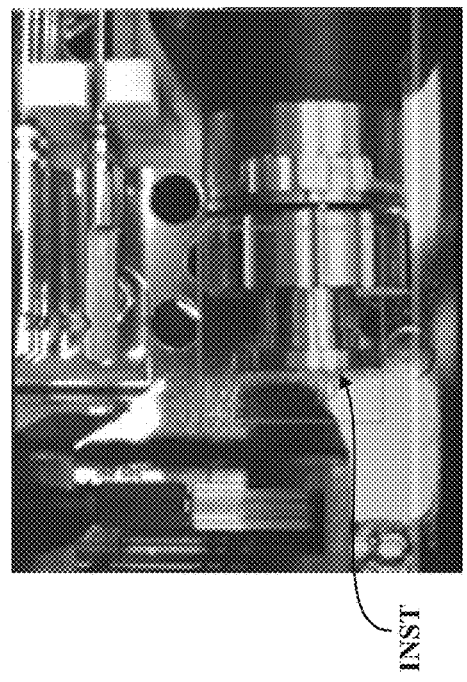
FIG. 7D
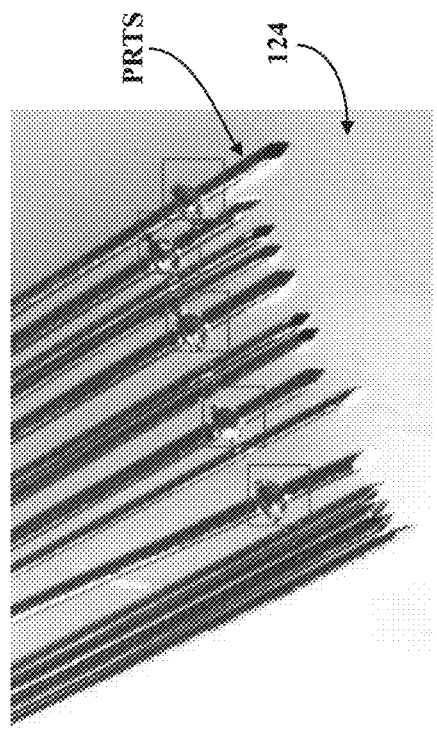
FIG. 7C

SURGICAL KIT INSPECTION SYSTEMS AND METHODS FOR INSPECTING SURGICAL KITS HAVING PARTS OF DIFFERENT TYPES

CROSS-REFERENCE TO RELATED APPLICATIONS

This application claims priority to and the benefit of U.S. Provisional Patent Application No. 63/036,596, filed on Jun. 9, 2020, the disclosure of which is expressly incorporated by reference in its entirety.

TECHNICAL FIELD

The present disclosure relates, generally, to systems and methods for inspecting kits having parts of different types.

BACKGROUND

Surgical kits include parts of different types that assist in performing surgical procedures. The parts may include implants, reusable parts (e.g., surgical instruments), and disposable parts. Usually, some parts (e.g., some of the implants and disposable parts) are consumed during the surgical procedure. The reusable parts may be damaged or worn or may have been inadvertently discarded or misplaced. For these reasons, after the surgical procedure has been performed, any surgical kits used in performing the surgical procedure need to be inspected to determine which parts are missing, damaged, or worn.

Once the used surgical kit is received at an inspection location, the inspection procedure involves discarding disposable parts (if any), comparing the parts in the used surgical kit against a list of parts that makeup a complete surgical kit, and inspecting each part of the used surgical kit for damage or wear, and to ensure proper placement of the part within the surgical kit. Once the inspection procedure is complete, missing, damaged, and/or worn parts are replaced, and the surgical kit is processed (e.g., sterilized) to be ready for the next surgical procedure.

Some inspection procedures are still, in large part, performed manually by an operator. The process may begin, for example, by the operator printing off the list of parts that makeup a complete surgical kit. The operator then manually inspects every part in the used surgical kit and compares the parts to the list. The operator marks the used surgical kit as "complete" when no items are missing or "as is" when there are missing parts. The operator may also visually inspect the parts for damage or wear. The operator creates a list of missing, damaged, and/or worn parts through an inventory system and parts may subsequently be replaced. Manual inspection by the operator of every part is time consuming and prone to operator error.

SUMMARY

A surgical kit inspection system is provided for inspecting surgical kits having parts of different types. The surgical kit inspection system comprises a first camera unit having a first lens to obtain images of unique geometric features of parts of a first type and a second camera unit having a second lens, different than the first lens, to obtain images of characters on parts of a second type. A robotic manipulator supports the first and second camera units such that the first and second camera units are capable of being moved by the robotic manipulator relative to the surgical kits. One or more controllers are configured to: obtain unique inspection instructions for each of the surgical kits to control inspection of each of the surgical kits; position the robotic manipulator at a plurality of poses relative to each of the surgical kits in accordance with the unique inspection instructions; operate one or both of the first camera unit and the second camera unit at each of the plurality of poses to capture images at each of the plurality of poses; detect parts in the images captured at each of the plurality of poses using a first identification method when utilizing the first camera unit and using a second identification method when utilizing the second camera unit; compare the detected parts for each of the surgical kits to a predefined list of parts for each of the surgical kits; and generate output indicating inspection results for each of the surgical kits.

A method is provided for inspecting surgical kits having parts of different types using a robot and a vision unit supported by the robot. The vision unit has a first camera unit and a second camera unit. The method comprises obtaining unique inspection instructions for each of the surgical kits to control inspection of each of the surgical kits. The method also comprises positioning the robot at a plurality of poses relative to each of the surgical kits in accordance with the unique inspection instructions. The first camera unit and the second camera unit move relative to each of the surgical kits during the positioning of the robot at the plurality of poses. One or both of the first camera unit and the second camera unit are operated at each of the plurality of poses to capture images at each of the plurality of poses, wherein the first camera unit has a first lens to obtain images of unique geometric features of parts of a first type and the second camera unit has a second lens, different than the first lens, to obtain images of characters on parts of a second type. Parts are detected in the images captured at each of the plurality of poses using a first identification method when utilizing the first camera unit and using a second identification method when utilizing the second camera unit. The detected parts in each of the surgical kits are compared to a predefined list of parts for each of the surgical kits and output is generated indicating the inspection results for each of the surgical kits.

An inspection system is provided for inspecting kits having parts of different types. The inspection system comprises a vision unit including one or more camera units configured to obtain images of unique geometric features of parts of a first type and obtain images of characters on parts of a second type. A robotic manipulator supports the vision unit such that the vision unit is capable of being moved by the robotic manipulator relative to the kits. One or more controllers are configured to: obtain unique inspection instructions for each of the kits to control inspection of each of the kits; position the robotic manipulator at a plurality of poses relative to each of the kits in accordance with the unique inspection instructions; operate the one or more camera units at each of the plurality of poses to capture images at each of the plurality of poses; detect parts in the images captured at each of the plurality of poses using at least one of a first identification method and a second identification method; compare the detected parts in each of the kits to a predefined list of parts for each of the kits; and generate output indicating inspection results for each of the surgical kits.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

FIGS. 7A-7D are images of parts in a surgical kit captured by the vision unit.

In the drawings, reference numbers may be reused to identify similar and/or identical elements.

DETAILED DESCRIPTION

Figure 1:
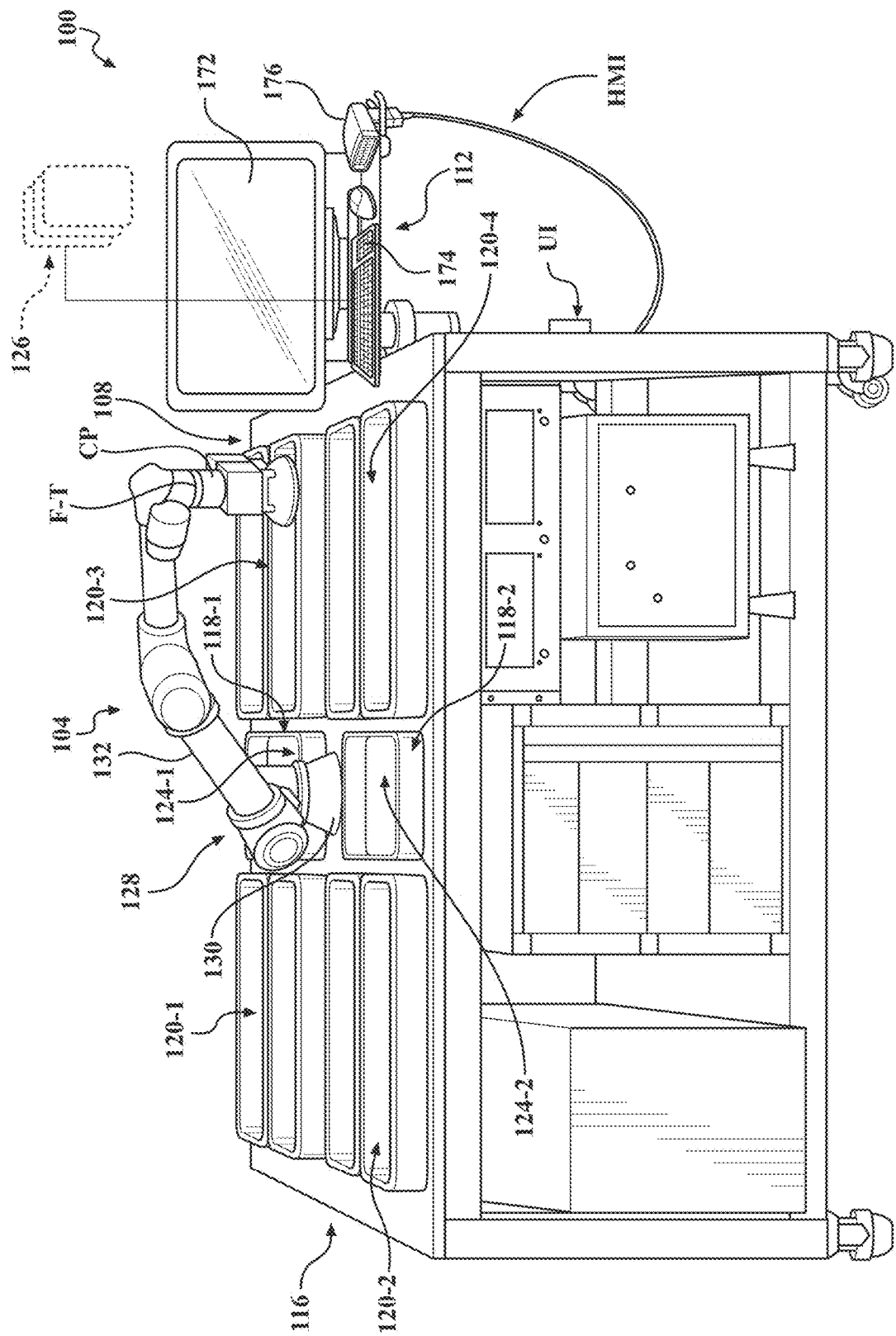
FIG. 1 is a perspective view of an example inspection system.

With reference to FIG. 1, an inspection system 100 is presented. The inspection system 100 provides a workstation including a robot 104, a vision unit 108, a working table 116 having zones 120, light surface units 118 having light surfaces 124, and a human machine interface HMI that allows an operator to interface with the inspection system 100. The inspection system 100 works in collaboration with the operator to inspect and inventory surgical kits. The inspection system 100 may also be referred to as a semi-automated inspection system. The inspection system 100 may be employed by vendors that supply the surgical kits to users of the surgical kits (e.g., hospitals, etc.) or the inspection system 100 may be employed by the users themselves.

The inspection system 100 receives used surgical kits and inspects the used surgical kits in conjunction with the operator based on an electronic kit inspection recipe 126 to identify missing, damaged, worn, and/or misplaced parts. The kit inspection recipe 126 may be stored in a database DB, such as local databases, cloud-based databases, or other type of database. The kit inspection recipe 126 provides information regarding all the parts required for a complete surgical kit and information as to how the robot 104, the vision unit 108, and/or the light surface units 118 are to be positioned and/or operated when inspecting each part, and which identification methods are to be employed to inspect each of the parts. Once the inspection procedure is complete, the inspection system 100 generates and stores output (e.g., an electronic inspection report) indicating which parts are missing, damaged, and/or worn. In some cases, the inspection reports may be electronically transmitted to a surgical kit management system, an enterprise resource planning (ERP) system, and/or a warehouse management system (WMS), to update a bill of materials for each of the surgical kits. This may be done automatically or in response to user input via the human machine interface HMI. The human machine interface HMI and one or more of these systems may be integrated to communicate with each other. Missing, damaged, and/or worn parts can then be replaced, and the surgical kit processed (e.g., sterilized) to be ready for the next surgical procedure. The inspection system 100 reduces the possibility for operator error and thus provides an improved way of inspecting surgical kits. It should be appreciated that although the inspection system 100 is described throughout for inspecting surgical kits, it may also be used for inspecting kits other than surgical kits.

The robot 104 includes a robotic manipulator 128 having a base 130 and a robotic arm 132 extending from the base 130. The robotic manipulator 128 supports and carries the vision unit 108 to move the vision unit 108 to a plurality of different poses in view of the each of the parts being inspected for each of the surgical kits. The base 130 of the robotic manipulator 128 may be mounted to the working table 116 at the center of the working table 116 or at any other suitable position where the robotic manipulator 128 is able to position the vision unit 108 in view of each of the zones 120. In some versions, the robotic manipulator 128 may include additional robotic arms 132, or any other suitable robotic structure to move the vision unit 108. In the version shown, the robotic arm 132 is a serial robotic arm. Parallel robotic arms, or any other suitable mechatronic structure for moving the vision unit 108 may be employed.

Figure 2:
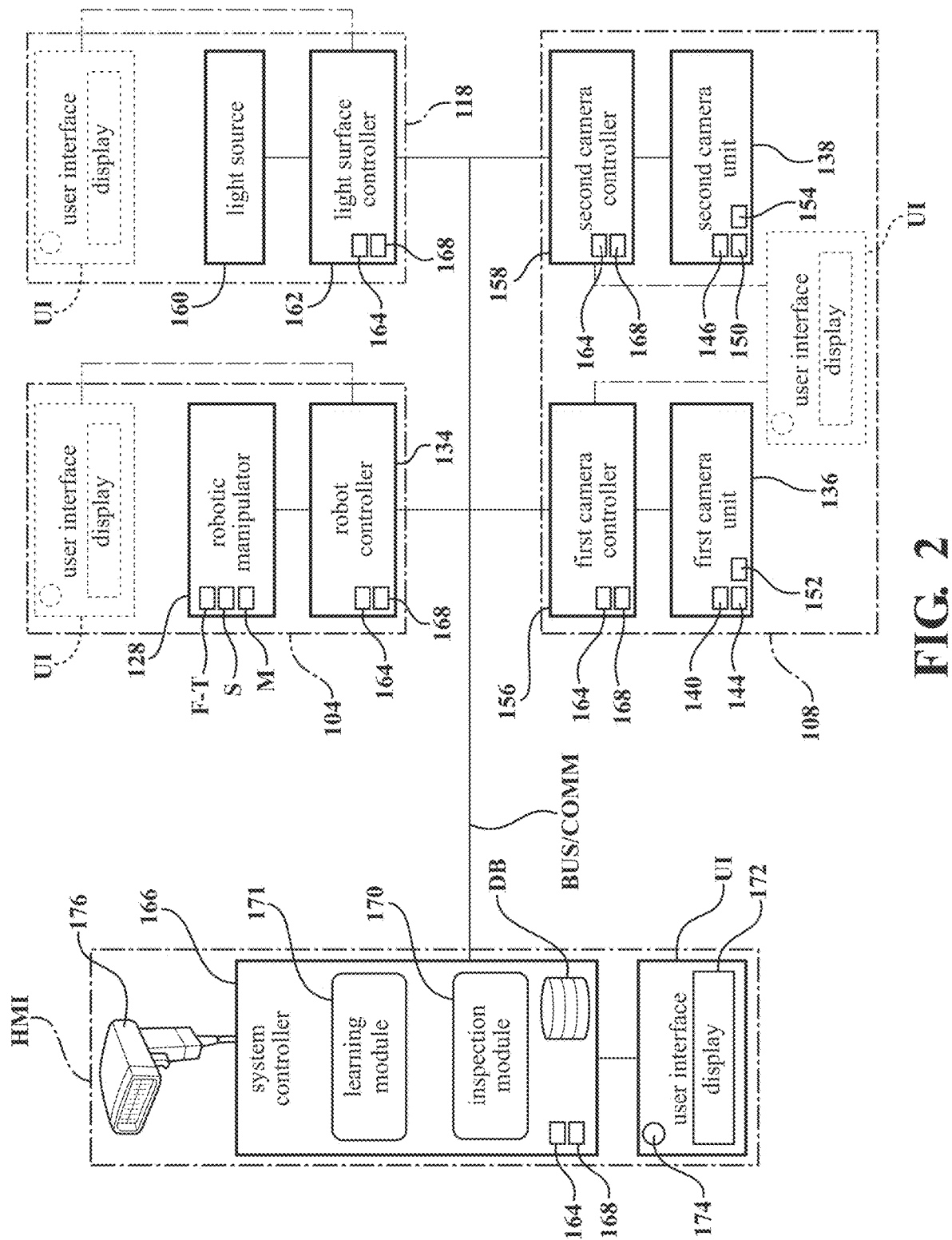
FIG. 2 is a block diagram of a control system of the inspection system.

As shown in FIG. 2, a robot controller 134 controls movement of the robotic manipulator 128 based on robot positioning instructions embodied in the kit inspection recipe 126 and based on operator input. The robot controller 134 may control positioning of the robotic manipulator 128, and by extension, the vision unit 108, by sensing a current pose (position and orientation) of the robotic manipulator 128 and/or vision unit 108 at each processing time step (e.g., frame) and determining a new commanded pose to which to move the robotic manipulator 128 and/or vision unit 108 based on the kit inspection recipe 126. The current pose and the new commanded pose may be defined with respect to a coordinate reference frame, such as a coordinate reference frame of the robotic manipulator 128 (e.g., fixed to its base 130), a coordinate reference frame of the vision unit 108 (e.g., associated with a moving tool center point (TCP) of the vision unit 108), or a coordinate reference frame of a tray of the surgical kit. Registration and calibration processes can be used to transform coordinates in one coordinate reference frame to another. As described further below, in some versions, the coordinate reference frame of the robotic manipulator 128 and/or the vision unit 108 are transformed to the coordinate reference frame of the tray being inspected (or vice versa) so that the robot controller 134 is able to accurately position the vision unit 108 relative to the parts in the tray.

The robot controller 134 determines how to move one or more joints of the robotic manipulator 128 (via joint motors M) to achieve movement to the new commanded pose. The robotic manipulator 128 may have position sensors S (e.g., joint and/or motor encoders) at each of the joints to determine the current pose of the robotic manipulator 128 in the coordinate reference frame of the robotic manipulator 128 via kinematic data associated with the robotic manipulator 128. The robot controller 134 can thereby also determine the current pose of the vision unit 108 (e.g., the TCP thereof) attached to the robotic manipulator 128 in the coordinate reference frame of the robotic manipulator 128 via a known and stored geometric relationship between the vision unit 108 (e.g., its TCP) and the robotic manipulator 128, which can be determined during manufacturing or via a calibration procedure. The robot controller 134 may instruct the robotic manipulator 128 to perform a sequence of movements to position the vision unit 108 in one or more poses as dictated by the kit inspection recipe 126 for each surgical kit. The kit inspection recipe 126 may provide a predefined set (and sequence) of poses to which to move the robotic manipulator 128 in one of the coordinate reference frames previously mentioned. The predefined set (and sequence) of poses can be determined by teaching the robotic manipulator 128 the poses (and sequence) via a teach pendant, and/or by programming the poses via other methods. In some versions, the robot 104 may be a model UR5e robot manufactured by Universal Robots of Denmark.

The robot 104 may also include one or more sensors to detect operator applied forces and torques. In the version shown, a force-torque sensor F-T is attached to a coupling CP (see FIG. 1) of the robotic arm 132. The vision unit 108 is attached to the coupling CP. The force-torque sensor F-T interconnects the coupling CP and the remaining portions of the robotic arm 132 so that the force-torque sensor F-T can detect forces and torques applied to the vision unit 108 by the operator. The force-torque sensor F-T may be a six degree-of-freedom type force-torque sensor to measure forces and torques in six degrees of freedom. Additionally, or alternatively, one or more torque sensors may be located at each joint of the robotic manipulator 128 to measure external forces and torques. The robotic manipulator 128 may have six joints to move the vision unit 108 in six degrees of freedom. When the operator wishes to manually cause movement of the robotic manipulator 128, the operator may apply forces and torques on the vision unit 108. As a result, the force-torque sensor F-T measures the forces and torques and sends corresponding output to the robot controller 134. The robot controller 134 is then able to evaluate the force and torques to determine a new commanded pose for the vision unit 108 based on the measurements, thereby effectively causing movement of the robotic manipulator 128 in a manner expected by the operator. Such collaborative robotic arms are well-known for responding to user-applied forces and torques.

Figure 3A:
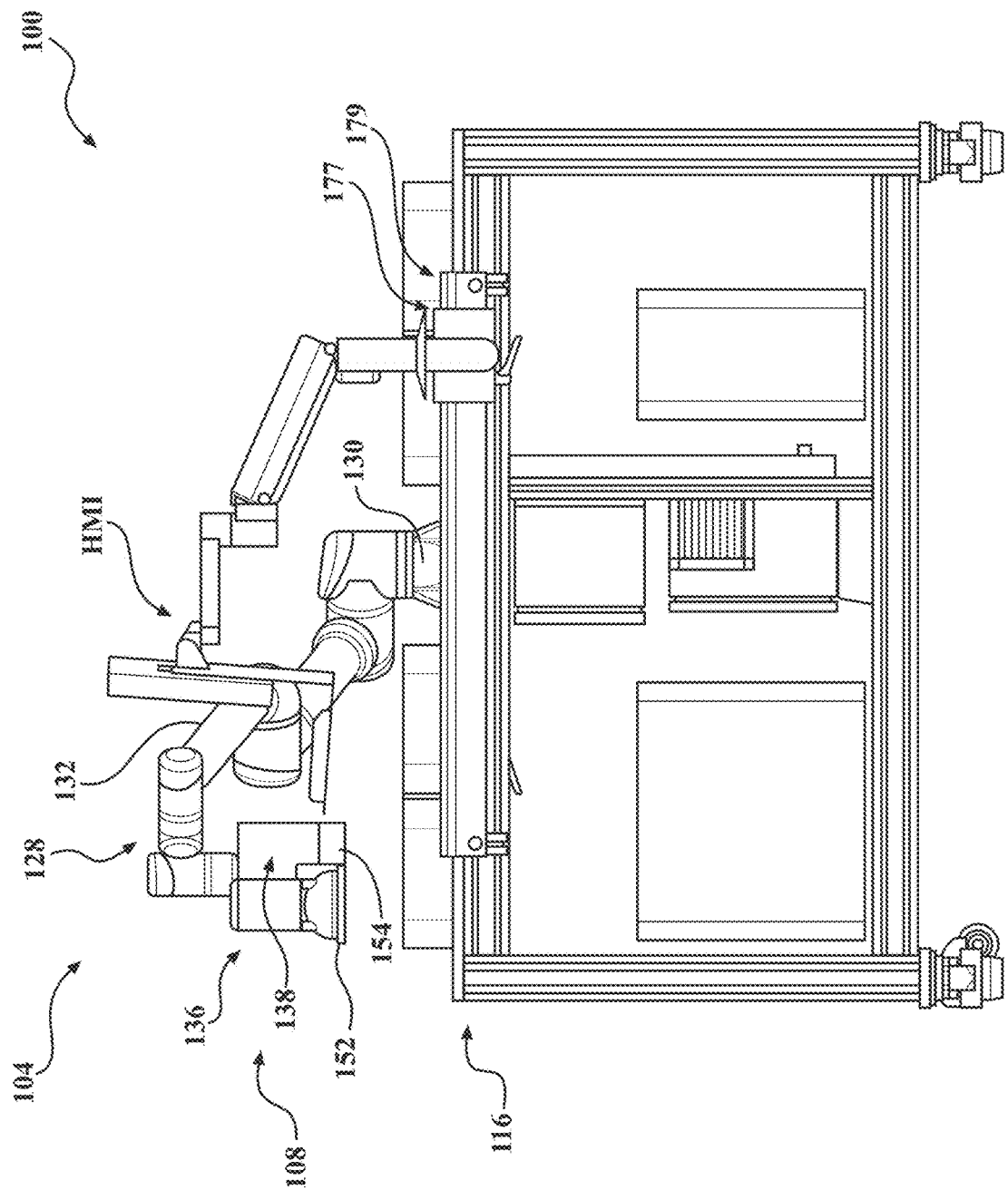
FIG. 3A is an elevational view of the inspection system of FIG. 1.
Figure 3B:
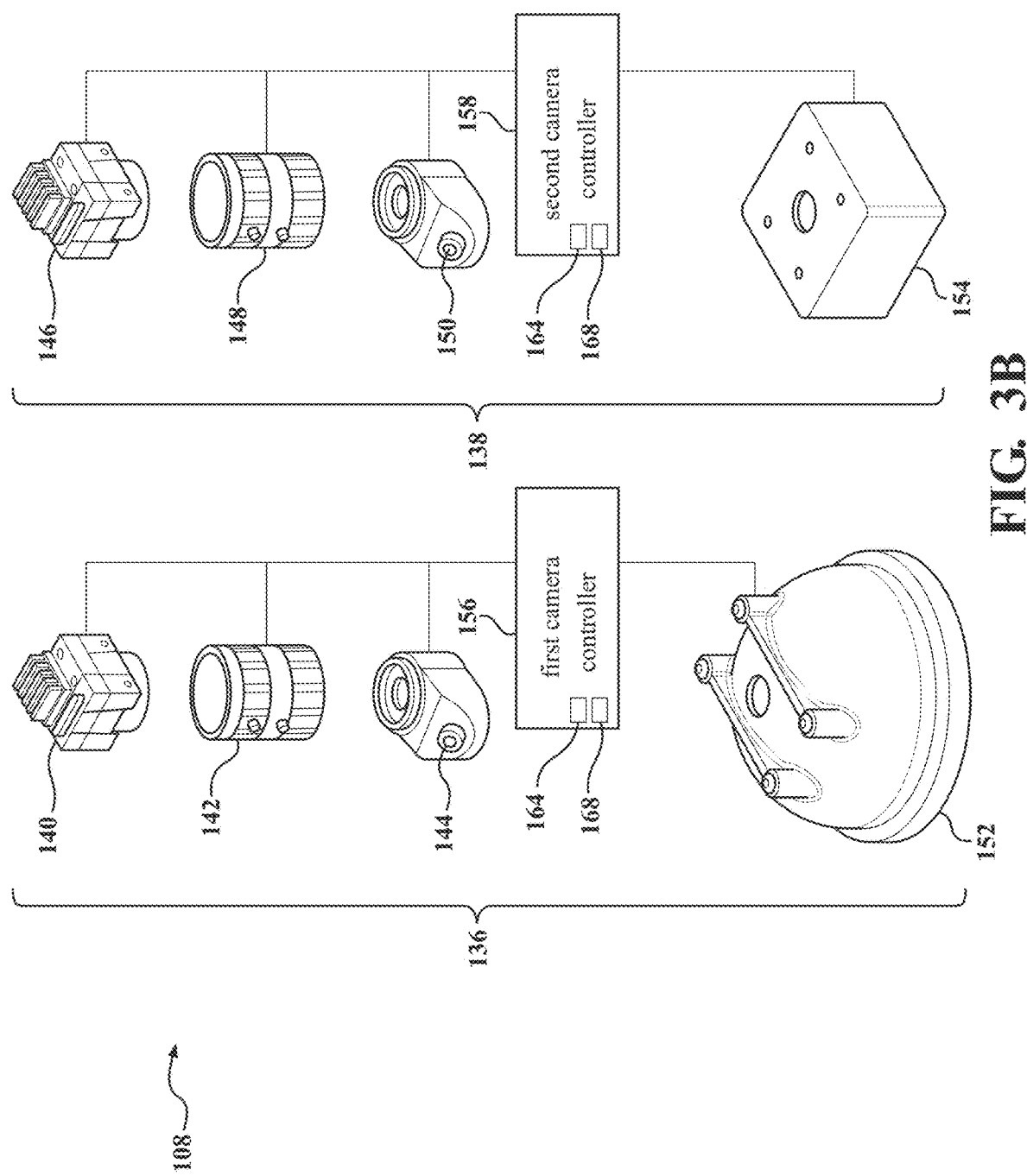
FIG. 3B is a partially exploded view of the vision unit.
Figure 3C:
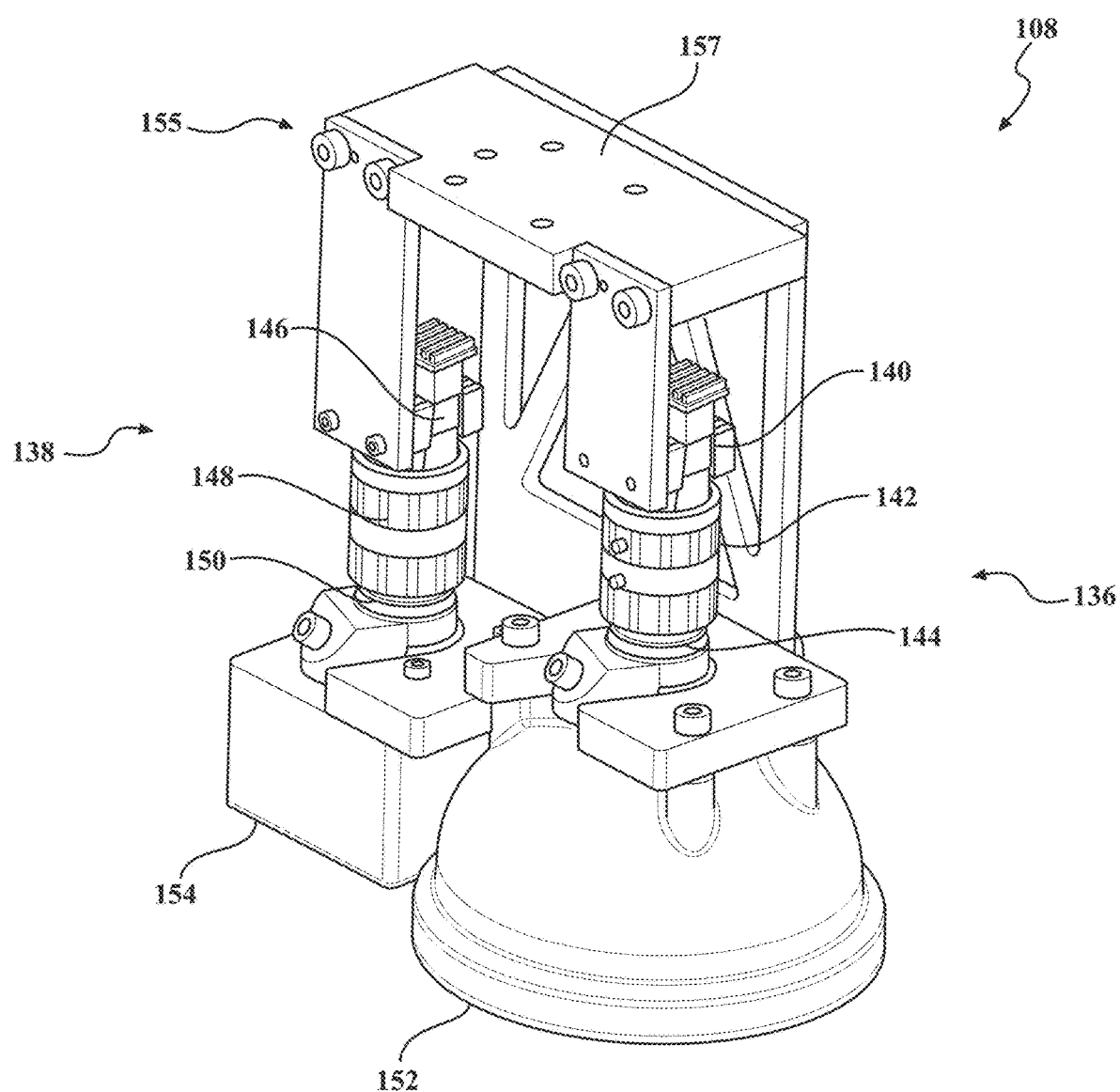
FIG. 3C is an assembled view of the vision unit.

With reference to FIGS. 3A through 3C, the vision unit 108 includes one or more camera units to capture images of the parts of the surgical kits. In the version shown, the vision unit 108 includes a first camera unit 136 and a second camera unit 138. The first camera unit 136 may be configured to capture images of parts of a first type under dynamic conditions such as when lighting conditions are changing or working distances are changing. The first camera unit 136 may include one or more cameras (e.g., machine vision cameras) and one or more lenses, including fixed focal length lenses, and lenses for automated adjustment of focal length and aperture. In some versions, referring to FIG. 3B, the first camera unit 136 includes a first camera 140, a first imaging lens 142 having a fixed focal length (e.g., 16 mm), and a first liquid lens 144 having a variable focus. In some examples, the first camera unit 136 may include camera model: CAM-CIC-5000-17-GC, manufactured by Cognex Corporation of Natick, Mass. with an ENMT lens manufactured by Opto-Engineering of Mantova, Italy. In some versions, the first camera unit 136 may include camera model: Alvium 1800 U-129C, manufactured by Allied Vision Technologies GmbH of Stadtroda, Germany with a 16 mm imaging lens, model: C-series #59-870 and a liquid lens, model: EL-10-30-Ci-VIS-LD-MV from Optotune Switzerland AG of Dietikon, Switzerland.

The second camera unit 138 may be configured to capture or read text, symbols, or other characters associated with parts of a second type. For example, the second camera unit 138 may be configured to read etched or laser marked part numbers on implants, such as screws. The second camera unit 138 may include one or more cameras (e.g., machine vision cameras) and one or more lenses, including fixed focal length lenses, and lenses for automated adjustment of focal length and aperture. In some versions, the second camera unit 138 includes a second camera 146, a second imaging lens 148 having a fixed focal length (e.g., 35 mm), different than the first imaging lens 142, and a second liquid lens 150 having a variable focus. The second camera unit 138 may also include a specialty lens configured to allow for magnification up to a predetermined factor. The predetermined factor may be equal to 1.5 times or any other suitable factor. In some examples, the second camera unit 138 may include camera model: CAM-CIC-5000-17-GC manufactured by Cognex Corporation of Natick, Mass. with a MC150X lens manufactured by Opto-Engineering of Mantova, Italy. In some versions, the second camera unit 138 may include camera model: Alvium 1800 U-129, manufactured by Allied Vision Technologies GmbH of Stadtroda, Germany with a 35 mm imaging lens, model: C-series #59-872 and a liquid lens, model: EL-10-30-Ci-VIS-LD-MV from Optotune Switzerland AG of Dietikon, Switzerland.

In some versions, the vision unit 108 may include one or more light sources to illuminate the parts of the surgical kits to improve imaging of the parts. For example, a first light 152 may be mounted to the robotic manipulator 128 as part of the first camera unit 136. The first light 152 may be model: DL194-WHI-I3S, manufactured by Advanced Illumination of Rochester, Vt. to generate diffuse, white, strobed light when capturing images with the first camera 140. A second light 154 may be mounted to the robotic manipulator 128 as part of the second camera unit 138. The second light 154 may be model: DL2230-WHI-I3S, manufactured by Advanced Illumination of Rochester, Vt. to generate diffuse, white, strobed light when capturing images with the second camera 146.

The vision unit 108 includes one or more camera controllers to control operation of the vision unit 108. In the version shown, the vision unit 108 includes a first camera controller 156 to control the first camera unit 136 and a second camera controller 158 to control the second camera unit 138. The camera controllers 156, 158 are coupled to their respective cameras 140, 146, liquid lenses 144, 150, and lights 152, 154 to control operation thereof in accordance with the kit inspection recipe 126.

As shown in FIG. 3C, the vision unit 108 has a support structure 155 with a mounting plate 157 that is mounted to the distal end of the robotic arm 132 of the manipulator 128. The support structure 155, in the embodiment shown, has a plurality of mounting plates and brackets to which the components of the camera units 136, 138 are mounted. The camera units 135, 138 are thus supported by the support structure to move with the manipulator 128.

The working table 116 has one or more working surfaces to support the surgical kits during inspection. The working table may include lockable casters, storage, and guides to help orient trays on the working surface. In some versions, the working table 116 and/or other portions of the workstation may be formed at least partially of Formica. This may be helpful, for example, to avoid interference with RFID readers that could be placed all around the workstation (at the sides/above/below) to automatically identify tagged parts (e.g., with RFID tags) placed on the working table 116 at the workstation. The tagged parts could be set on the working surface of the working table 116 (either directly or in a container) and then automatically counted. In this case, the inspection system 100 would be able to identify the tagged parts that are present and compare to a list of tagged parts that should be present in the surgical kit. In some versions, the working table 116 is formed primarily of stainless steel and the inspection system 100 operates without reading any tagged parts.

The light surface units 118 with light surfaces 124 are provided to assist in inspecting loose parts PRTS from each of the surgical kits. As shown in FIG. 1, the light surface units 118 may include a first light surface unit 118-1 having a first light surface 124-1 and a second light surface unit 118-2 having a second light surface 124-2. The first light surface 124-1 and the second light surface 124-2 may be arranged at opposing sides of the workstation. The first light surface 124-1 may be arranged between a first zone 120-1 and a third zone 120-3 while the second light surface 124-2 may be arranged between a second zone 120-2 and a fourth zone 120-4; however, other configurations are contemplated. The light surfaces 124 may form an upper surface of the light surface units 118 shaped to receive the loose parts PRTS and contain the loose parts PRTS to keep them on the light surface 124. The light surface units 118 may also be referred to as light tables, light containers, or light boxes.

Figure 4A:
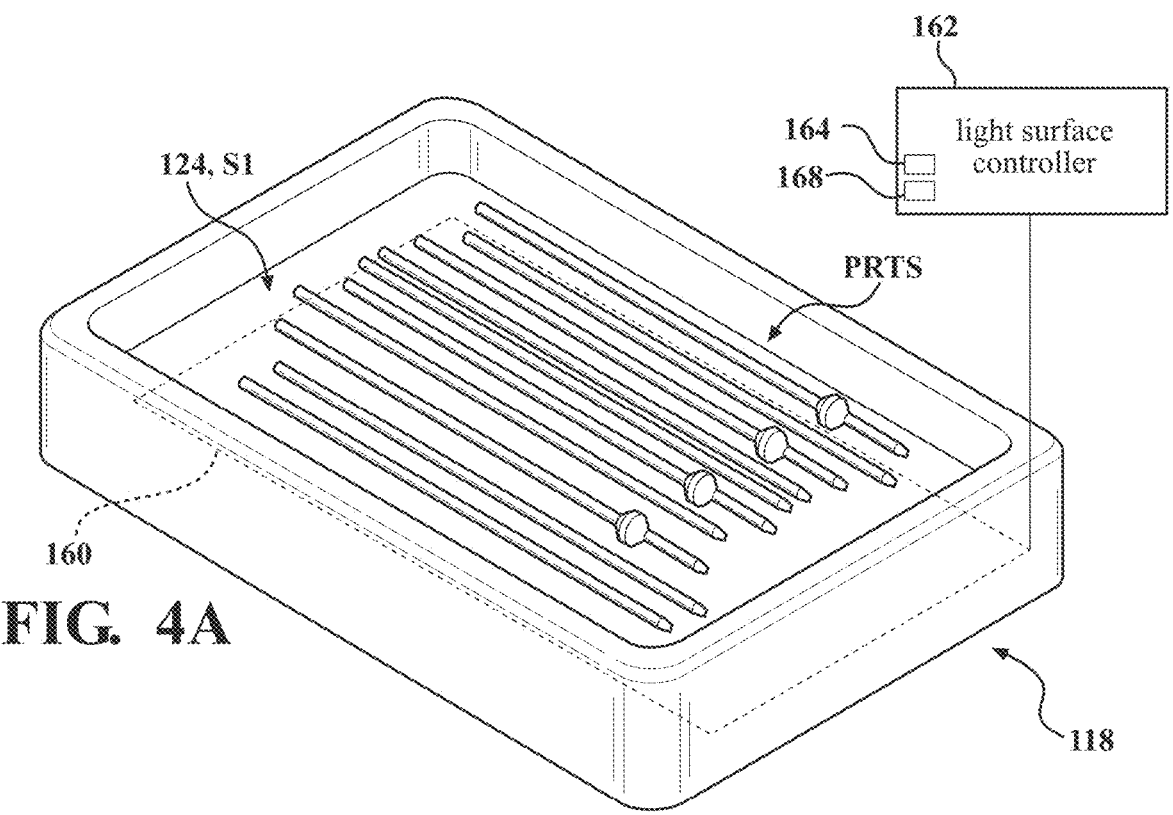
FIGS. 4A and 4B are perspective views of loose parts of a surgical kit set up on a light surface.
Figure 4B:
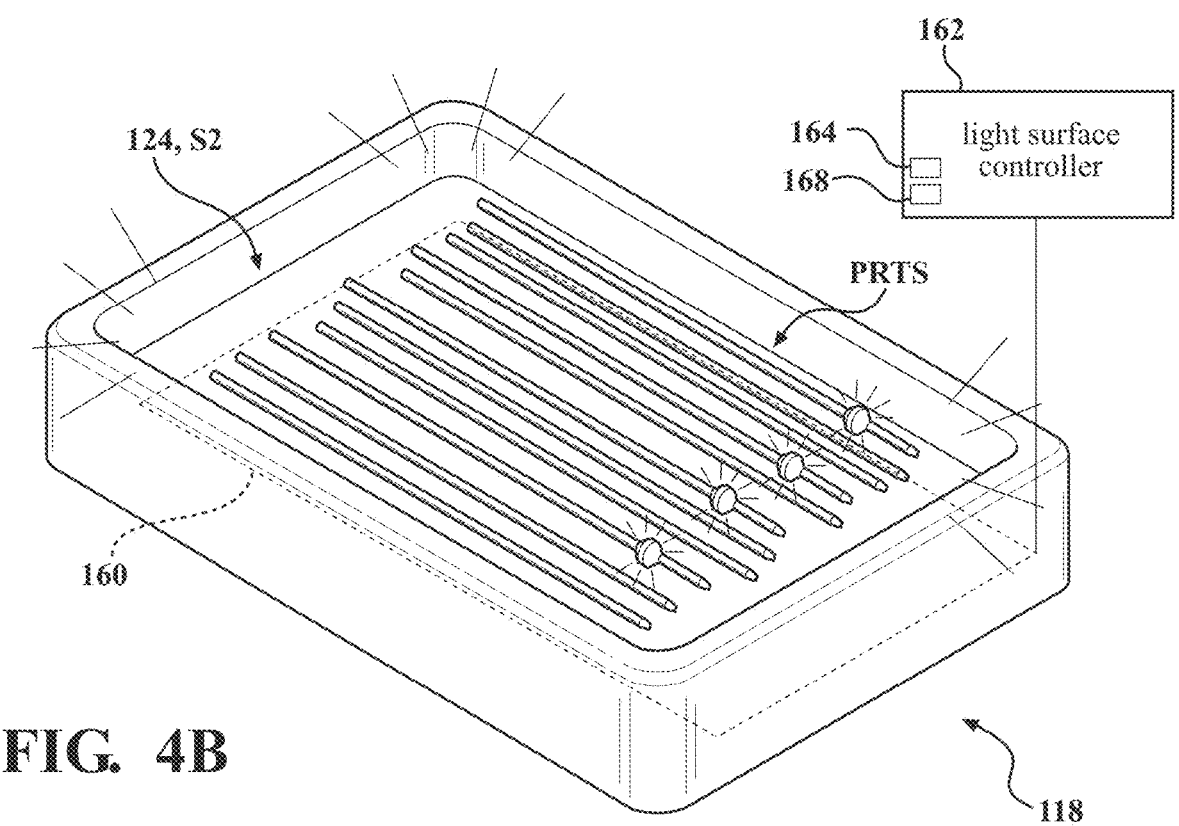

Referring to FIGS. 4A and 4B, each light surface unit 118 may include a light source 160, such as one or more white LED backlights and/or any other suitable light(s), configured to illuminate the light surfaces 124 and the loose parts PRTS from beneath the light surfaces 124 for enhanced imaging of the loose parts PRTS placed on the light surfaces 124. FIGS. 4A and 4B show a light surface 124 in a first state S1 (FIG. 4A) in which the light surface 124 is not illuminated by the light source 160 and in a second state (FIG. 4B) in which the light surface 124 is illuminated by the light source 160 to allow for better imaging (e.g., better contrast) to make identification via the inspection system 100 easier owing to the improved images captured by the vision unit 108 due to the light source 160.

The light surface units 118 include one or more light surface controllers to control operation of the light surface units 118. In the version shown, each light surface unit 118 has a separate light surface controller 162, but a single light surface controller could control all the light surface units 118. The light surface controllers 162 are coupled to their respective light sources 160 to control operation thereof in accordance with the kit inspection recipes 126. As described in greater detail below, each kit inspection recipe 126 may include instructions for relevant settings/states for the light sources 160 of the light surface units 118 (e.g., active, inactive, etc.). In some cases, the operator may control the light surface units 118 via input received by the light surface controllers 162.

Referring to FIG. 2, a block diagram of a control system of the inspection system 100 is depicted. The human machine interface HMI may use software or firmware to implement the techniques and/or methods introduced herein. The software or firmware may be stored on a non-transitory computer readable medium or memory 164. The human machine interface HMI includes a system controller 166 to control operation of the human machine interface HMI and the inspection system 100. The system controller 166 may be embodied in a computer system that runs the software for the robot 104, the vision unit 108, and/or the light surface units 118. The system controller 166 includes one or more processors 168 to execute one or more software modules/programs, such as an inspection module 170. In some versions, the system controller 166 may employ a learning module 171, which may be realized as a part of the inspection module 170 or may otherwise communicate with the inspection module 170 or other portions of the system controller 166. These software modules/programs collaborate to receive and or transmit data to the robot controller 134, camera controllers 156, 158, and/or light surface controllers 162, via any suitable communication protocol. Each of the robot controller 134, camera controllers 156, 158, and light surface controllers 162 may have their own memory 164 and one or more processors 168 and may coordinate with the system controller 166 to implement the techniques and/or methods described herein. More or fewer controllers may be used in the control system. In some versions, the system controller 166 controls and operates the robot 104, the vision unit 108, and/or the light surface units 118. In some versions, collectively, the system controller 166, robot controller 134, camera controllers 156, 158, and/or light surface controllers 162 may be embodied in one or more computers.

The inspection module 170 may be configured to provide inspection instructions by transmitting associated instructions based on the kit inspection recipes 126 to the robot controller 134, camera controllers 156, 158, and/or the light surface controllers 162. Each of the kit inspection recipes includes a unique set of instructions for the robot controller 134, camera controllers 156, 158, and/or the light surface controllers 162 to control the robotic manipulator 128, camera units 136, 138, and light surface units 118 during inspection of surgical kits. For instance, each surgical kit has a unique kit inspection recipe 126 that includes various instructions for controlling the robotic manipulator 128 and the camera units 136, 138 based on a layout of the surgical kits. Once inspection of each of the surgical kits is complete, the inspection module 170 may receive kit inspection results (discussed in greater detail with respect to FIG. 8B) back from the robot controller 134 and/or camera controllers 156, 158 and store the kit inspection results in the one or more databases DB. The inspection module 170 may be configured to maintain the database DB of records pertaining to surgical kits including respective kit inspection recipes 126 for each surgical kit and an inspection history for each surgical kit including kit inspection results. Images associated with parts that were improperly identified and therefore resulted in a need for correction by the operator may be flagged. These images may be used as training images. The inspection module 170 and/or the learning module 171, as discussed in greater detail below, may be configured to learn from the flagged training images using one or more machine learning algorithms or models (e.g., an automated supervised learner model or a reinforcement learner model) to increase a rate at which the inspection system 100 is correctly identifying parts within surgical kits, as well as to otherwise optimize control of the robotic manipulator 128, camera units 136, 138, and light surface units 118 during inspection of surgical kits.

The operator is configured to collaborate with the robot 104, the vision unit 108, and/or the light surface units 118 via a user interface UI coupled to the system controller 166. In some versions, separate user interfaces UI may be coupled to each of the system controller 166, robot controller 134, camera controllers 156, 158, and/or light surface controllers 162. The user interfaces UI may each include one or more displays 172 (e.g., flat panel LED display, OLED display, etc.) and one or more user input devices 174 (e.g., touchscreen, keyboard, computer mouse, pushbuttons, foot pedals, sensors, gesture control, voice control, etc.) to facilitate interaction with the operator. For example, the inspection module 170, via a GUI on the display 172, may prompt the operator for certain information, as discussed in greater detail below, prior to, during, and subsequent to inspection of the surgical kits. The operator may provide input to the inspection module 170 via the GUI shown on the display 172.

A reader device 176 (e.g., barcode scanner, RFID tag reader) may be coupled to the system controller 166. The reader device 176 may include an optical scanner, one or more radio frequency antennas, etc. that can read and decode the barcodes, RFID tags, etc. from the surgical kits and provide identification information to the inspection module 170.

The user interface UI coupled to the system controller 166, and the reader device 176, may be slidably mounted to the working table 116 via a slider 177. A rail 179 fixed to the working table 116 slidably supports the slider 177 (see FIG. 3A). The user interface UI and the reader device 176 are mounted to and supported by the slider 177 such that the operator may slide the user interface UI and the reader device 176 as desired. Any suitable mounting system may be used. A second, slidable user interface UI and/or reader device 176 may be included on an opposite side of the working table 116, such as for processing multiple kits at the working table 116 and/or for multiple operators. In some cases, the same operator may process multiple kits at the working table 116 with multiple robots 104 and vision units 108 (not shown).

Figure 5:
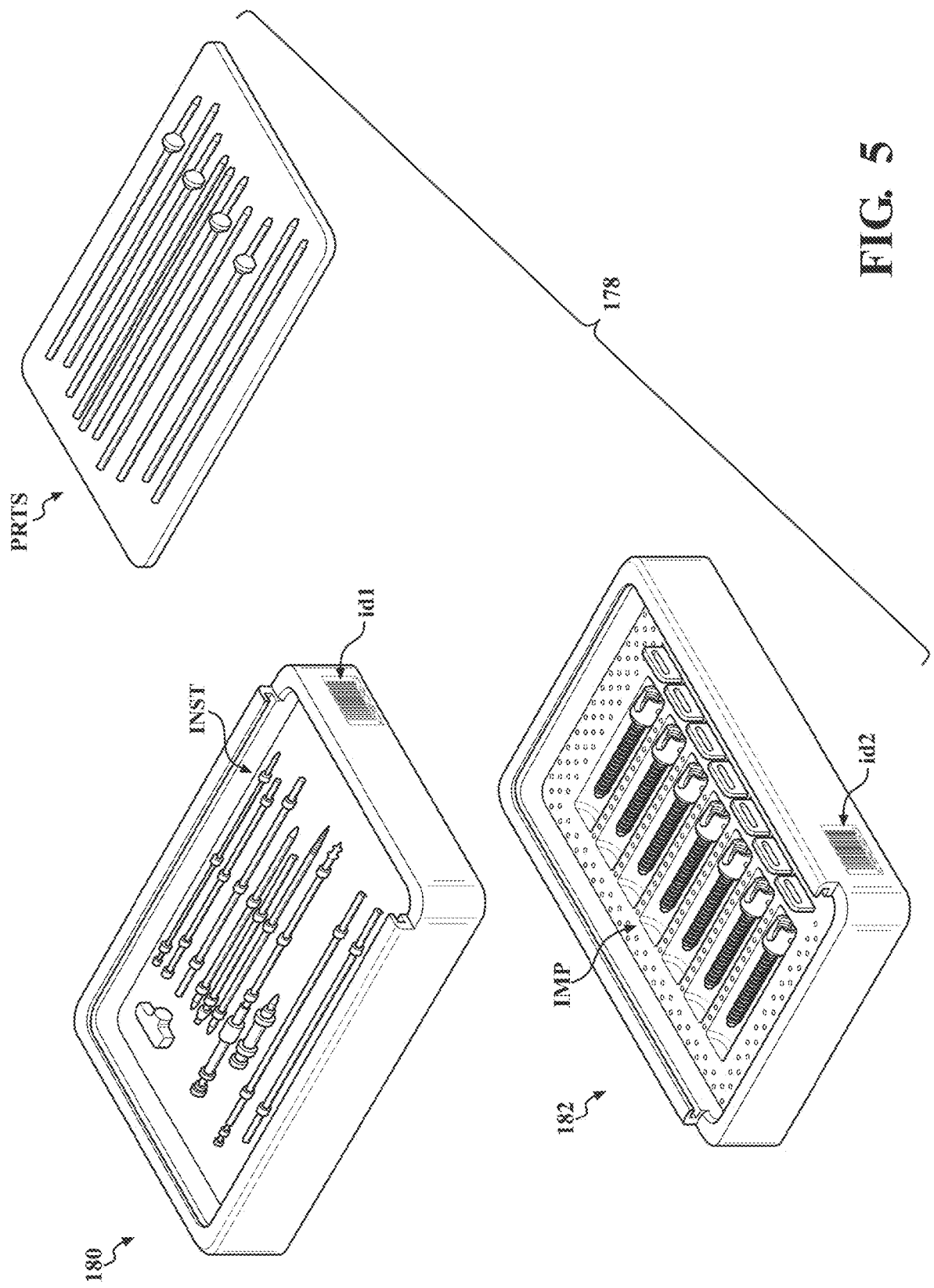
FIG. 5 illustrates perspective views of a first tray, a second tray, and loose parts of a surgical kit.

With reference to FIG. 5, an example surgical kit 178 is shown. The surgical kit 178 includes a first tray 180 with surgical instruments INST, a second tray 182 with surgical implants IMP, and loose parts PRTS. While, in the example provided, the surgical kit 178 includes the two trays, 180, 182 and loose parts PRTS, the surgical kit 178 may include any number of trays and any number of loose parts. In surgical kits where there is only one tray and no loose parts, a surgical tray and a surgical kit are the same for practical purposes. The first tray 180 may include a first unique identifier id1 (e.g., embodied in a bar code, RFID tag, etc.) and the second tray 182 may include a second unique identifier id2 (e.g., embodied in a bar code, RFID tag, etc.). The first and/or second unique identifiers id1, id2 may be scanned by the reader device 176 and used by the inspection module 170 to retrieve a matching surgical kit inspection recipe 126 and associated instructions. The first unique identifier id1 and the second unique identifier id2 may be the same to identify the surgical kit, may be different to uniquely identify each tray, and/or may uniquely identify the tray and the surgical kit.

The inspection module 170 retrieves and provides the inspection system 100 with the kit inspection recipe 126 in response to the human machine interface HMI receiving the unique identifier id1 and/or id2 associated with the surgical kit. For example, the operator may scan into the human machine interface HMI, a barcode (or another suitable unique identifier) associated with the surgical kit via the reader device 176. The human machine interface HMI uses the scanned barcode to determine the associated id and the inspection module 170 retrieves the kit inspection recipe 126 associated with the surgical kit. In some configurations, the surgical kit may include a barcode that is separate from the barcodes of any trays in the surgical kit. For the surgical kit 178, for example, the surgical kit may have an id that is separate from the unique identifiers id1, id2 of the first and second trays 180, 182 and that is separately scanned by the reader device 176 and used to retrieve the kit inspection recipe 126. In other configurations, each tray of the surgical kit 178 may have the same kit id (e.g., id1 and id2 are the same, or both identify the same surgical kit) and the human machine interface HMI may be configured to retrieve the kit inspection recipe 126 based on the first and/or second identifiers id1, id2 of the first and second trays 180, 182.

Figure 6:
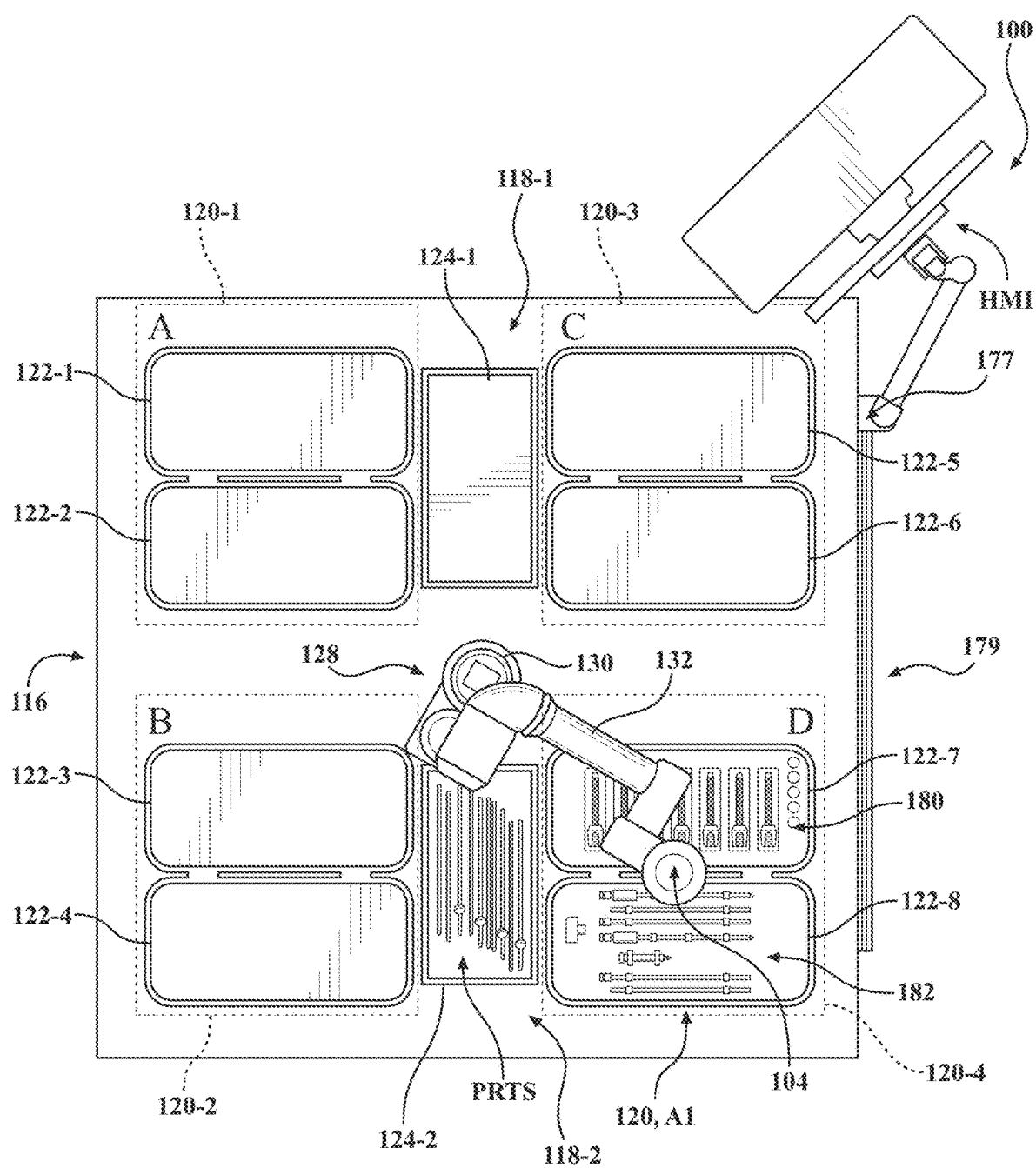
FIG. 6 is a top view of the inspection system of FIG. 1.

With reference to FIG. 6, the zones at which surgical trays may be inspected include the first zone 120-1, the second zone 120-2, the third zone 120-3, and the fourth zone 120-4. The first zone 120-1 may correspond to "Zone A", the second zone may correspond to "Zone B", the third zone may correspond to "Zone C", and the fourth zone 120-4 may correspond to "Zone D." Each of the zones 120 may include one or more bins 122. For example, the first zone 120-1 may include a first bin 122-1 and a second bin 122-2, the second zone 120-2 may include a third bin 122-3 and a fourth bin 122-4, the third zone 120-3 may include a fifth bin 122-5 and a sixth bin 122-6, and the fourth zone 120-4 may include a seventh bin 122-7 and an eighth bin 122-8.

The operator may load the one or more trays of the surgical kit into any of the zones and any loose parts PRTS can be placed onto one or more of the light surfaces 124-1, 124-2. For example, with respect to the surgical kit 178, the first tray 180 and the second tray 182 are in the seventh bin 122-7 and the eighth bin 122-8, respectively, in the fourth zone 120-4 (i.e., "Zone D") and the loose parts PRTS are set up on the second light surface 124-2. While the robot 104 is inspecting the surgical kit 178, the operator may set up additional surgical kits in the remaining zones 120-1, 120-2, 120-3, and on the other light surface 124-1.

During inspection, the inspection system 100 captures one or more images of the parts in the surgical kit to determine one or more of the following for each part: (i) is the part present or missing; (ii) is the part in the proper location in the surgical kit (if there is a specific location at which the part is to be located); (iii) is the part damaged; (iv) is the part worn; and (v) how many times has the part been in the surgical kit. Any other characteristics of the parts can be determined by identifying the parts in the surgical kit.

Example images taken of the parts from the surgical kit 178 are shown in FIGS. 7A through 7D. In FIG. 7A, the first camera unit 136 was placed at a predefined pose relative to the first tray 180 based on the kit inspection recipe 126 and then employed to capture an image in which a part no. of a part (e.g., 703882) could be seen and electronically translated via optical character recognition (OCR). The inspection module 170 can compare the characters found in the image and translated via OCR to characters that the kit inspection recipe 126 indicates should be seen in the image captured at that pose to determine if there is a match. If there is a match, then the inspection system 100 indicates that the part is present. If there is no match, then the inspection system 100 indicates that the part is missing. In some cases, there may be a match, but the characters are found in a position and/or orientation not expected by the inspection module 170, i.e., the part is misplaced. The inspection system 100 may report the misplacement to the operator and once the inspection is complete, the operator may place all misplaced parts in their proper location.

In FIG. 7B, the second camera unit 138 was placed at a predefined pose relative to the second tray 182 based on the kit inspection recipe 126 and then employed to capture an image in which a part no. and/or lot code of a part (e.g., 657318 or v07603) could be seen and electronically translated via optical character recognition (OCR). In this example, the second camera unit 138 is used to provide high resolution images of small parts (e.g., a head of a 3.5 mm screw is shown). The inspection module 170 can compare the characters found in the image and translated via OCR to characters that the kit inspection recipe 126 indicates should be seen in the image captured at that pose to determine if there is a match. If there is a match, then the inspection system 100 indicates that the part is present. If there is no match, then the inspection system 100 indicates that the part is missing or misplaced.

In FIG. 7C, the loose parts PRTS are shown on the light surface 124 being back illuminated and the first camera unit 136 has captured an image of all the loose parts PRTS to count/identify which parts are present/missing. In this case, pattern recognition algorithms may again be used. For example, the image shown in FIG. 7C shows two types of parts, those with enlarged portions and those without. The kit inspection recipe 126 may provide one or more patterns expected to be seen in the image of the loose parts PRTS, including different patterns for different parts. For example, the kit inspection recipe 126 for the surgical kit 178 may provide a geometric pattern for the enlarged portion. The inspection system 100 can then count the number of enlarged portions that can be seen in the image via pattern matching the geometric pattern associated with the enlarged portion to the image and then counting how many times the pattern is found—five times in the example of FIG. 7C (as indicated by the pattern matching indicator boxes).

In FIG. 7D, the first camera unit 136 was placed at a predefined pose relative to the first tray 180 based on the kit inspection recipe 126 and then employed to capture an image of one of the instruments INST. The kit inspection recipe 126 provides one or more patterns (e.g., unique geometric shapes, etc.) expected to be seen in the image captured. The image is then processed via the inspection module 170 using pattern recognition algorithms to determine if any of the one or more patterns are found in the image. If the one or more patterns are found (matched) in the image, then the inspection system 100 indicates that the part is present. If no matches are found, then the inspection system 100 indicates that the part is missing. In some cases, there may be a match, but the pattern is found in a position and/or orientation not expected by the inspection module 170, i.e., the part is misplaced. The inspection system 100 may report the misplacement to the operator and once the inspection is complete, the operator may place all misplaced parts in their proper location. In FIG. 7D, the pattern matching indicator box indicates that the pattern was found in the image.

The kit inspection recipe 126 can dictate which camera unit 136, 138 to use to inspect each part, and the type of part identification used for each part (e.g., pattern recognition, OCR, and the like). In addition to identifying whether the part is present or missing, the inspection module 170 may also determine if the part is damaged (e.g., has one or more defects) or is worn. This may be accomplished by comparing the captured images to images of undamaged or unworn parts to find differences. This can also be accomplished by the one or more of the controllers 134, 156, 158, 162, 166 employing deep learning algorithms as an identification method to further inspect the parts in the surgical kit, such as may be facilitated by the learning module 171 or other parts of the system controller 166. In some versions, these types of deep learning algorithms may rely on training of neural networks using images of undamaged/unworn parts and/or images of damaged/worn parts, including parts that have nicks, scratches, etc. Accordingly, in some versions, one or more of the controllers 134, 156, 158, 162, 166 can analyze the parts to detect defects and can classify those defects (e.g., as a "scratch" or "nick", etc.). Both the first camera unit 136 and the second camera unit 138 can capture images that allow the inspection system 100 to identify such defects. The inspection system 100 can then utilize deep learning algorithms that are sufficiently trained to determine whether each of the parts is damaged, worn, etc. Furthermore, deep learning algorithms and methods may be employed to promote improved inspection of surgical kits by, among other things, optimizing control of of the robotic manipulator 128, camera units 136, 138, and/or light surface units 118 during inspection of specific parts. Deep learning algorithms and methods that may be employed by the inspection system 100 include those found in VisionPro® ViDi™ deep learning-based image analysis software from Cognex Corporation of Natick, Mass., including those utilized in VisionPro® ViDi™ v 3.1 and Vidi2. Deep learning algorithms and methods that may be employed by the inspection system 100 for pattern matching, string matching, detecting defects, and the like may include those described in U.S. Patent Application Pub. No. 2020/0005069 to Wang et al., entitled "System And Method For Finding And Classifying Patterns In An Image With A Vision System," filed on Jun. 6, 2019, which is hereby incorporated herein by reference.

As will be described further below, each kit inspection recipe 126 provides information to be transmitted to one or more of the controllers 134, 156, 158, 162, 166 as to how the robot 104, vision unit 108, and/or light surface units 118 are to move and/or operate to inspect each of the parts, such as each of instruments INST in tray 180, each of the implants IMP in tray 182, and each of the loose parts PRTS. Such information includes, for example: (i) the pose (i.e., coordinates x, y, z, u, v, w) to which the robotic manipulator 128 should move to capture one or more images of the part; (ii) which camera unit 136, 138 (e.g., one or both) should be operated at each pose to capture the one or more images of the part; (iii) one or more lens settings and/or lighting settings for the camera unit 136, 138 being operated; (iv) settings for the light surface unit 118, if used; and/or (iv) the identification method used to identify the part in the one or more images.

Figure 8A:
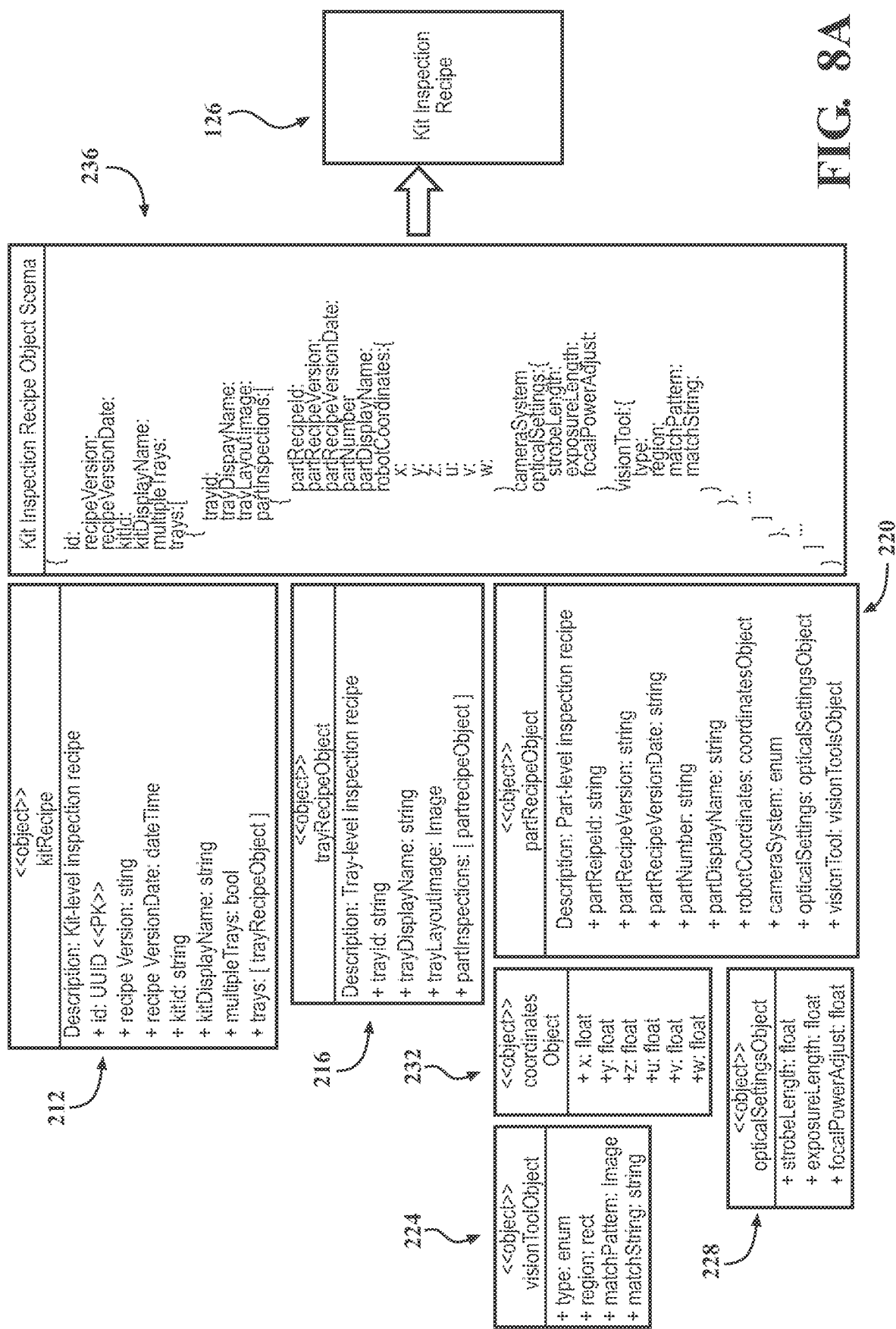
FIG. 8A is a block diagram of a kitRecipe class used to create a kit inspection recipe object for a surgical kit.

With reference to FIG. 8A, example block diagrams of various classes (i.e., program code templates) are shown for creating objects associated with the kit inspection recipe 126. The kit inspection recipe 126 may be created in advance based on operator input and is unique to each surgical kit. For surgical kits that are different, a separate kit inspection recipe 126 is provided. Once created, the kit inspection recipes 126 may be stored in the database DB or any suitable location for later retrieval by the inspection system 100. To start the inspection process, as described further below, the inspection system 100 retrieves the kit inspection recipe 126 based on the identification of the surgical kit being inspected. If there is no kit inspection recipe 126 for a surgical kit, then the operator must create a new kit inspection recipe 126.

An example block diagram of a kitRecipe class 212 is shown for creating the kit inspection recipe 126 (i.e., the kitRecipe class 212 is instantiated to create the kitRecipe object). The kitRecipe class 212 may include one or more variables such as id, recipeVersion, recipeVersionDate, kitId, kitDisplayName, and multipleTrays. The id variable may be assigned a unique identifier for each of the surgical kits (e.g., such as the unique identifiers id1, id2 for the surgical kit 178). The recipeVersion variable may be assigned a version of the kit inspection recipe 126, for example, "first version," "second version," etc. The kitId variable may be assigned a name indicative of the type of surgical kit, or may correlate to an existing part number for the kit, etc. The kitDisplayName variable may be assigned a name indicative of the type of surgical kit, which is to be displayed on the GUI of the inspection module 170. The kitId and the kitDisplayName may be the same in some cases. The multipleTrays variable may be assigned a boolean value, for example, with true indicating that multiple trays are present in the surgical kit and false indicating that there is just a single tray or only loose parts PRTS for a particular surgical kit. For example, the kit inspection recipe 126 for the surgical kit 178 would have this variable being assigned a true value since there are two trays 180, 182 and loose parts PRTS (also considered a "tray" in the kit inspection recipe 126.

The kitRecipe class 212 may also include a trayRecipe subclass 216. The inspection module 170 may use the trayRecipe subclass 216 to create a trayRecipeObject for each tray in the surgical kit and for the loose parts PRTS. For example, for the surgical kit 178, the trayRecipe subclass 216 would be instantiated to create three trayRecipeObjects for the kitRecipe object—one for the first tray 180, one for the second tray 182, and one for the loose parts PRTS.

The trayRecipe subclass 216 may include one or more variables such as trayID, trayDisplayName, and trayLayoutImage. The trayID variable may be assigned a unique identifier for each tray of the surgical kit (e.g., such as the unique identifiers id1, id2 for the surgical kit 178). The trayDisplayName may be assigned a name to be displayed for each tray on the GUI of the inspection module 170, for example for the first tray 180 the name shown on the GUI may correspond to "Instrument Tray." The trayLayoutImage may be assigned an image of a tray, for example an image of the first tray 180, second tray 182, etc. The trayRecipe subclass 216 may also include a subclass such as a partRecipe subclass 220.

The inspection module 170 may use the partRecipe subclass 220 to create a partrecipeObject for each part of a tray, for example, for each instrument INST in the first surgical tray 180, for each implant IMP in the second surgical tray 182, and collectively for the loose parts PRTS. Each partrecipeObject may include a unique set of instructions that the robot controller 134, the camera controllers 156, 158, the light surface controllers 162, and/or the system controller 166 use to control the robot 104 and the vision unit 108 to inspect each part in the surgical kit. The partRecipe subclass 220 may include variables such as partRecipeId, partRecipeVersion, partRecipeVersionDate, partNumber, partDisplayName, and partRecipeId. The partRecipeId may be assigned a unique identifier for each part of the surgical kit. The partRecipeVersion may be assigned a recipe version, for example, a first version, a second version, etc. The partRecipeVersionDate may be assigned a date and/or time that the corresponding version of the part recipe was created or generated. The partNumber variable may be assigned an existing part number of a part (e.g., serial number, etc.). The partDisplayName variable may be assigned a name of a part to be displayed on the GUI of the inspection module 170.

The partRecipe subclass 220 may also include one or more subclasses such as a visionTool subclass 224, an opticalSettings subclass 228, and a coordinates subclass 232. The coordinates subclass 232 may include variables x, y, z, u, v, and w that correspond to robot coordinates, including position (x, y, z) and orientation (u, v, w) for a coordinate reference frame, such as a coordinate reference frame associated with the tray in which the part resides. The inspection module 170 may use the coordinates subclass 232 to create a coordinatesObject for each part in a tray, for example, each instrument INST in the first tray 180 or for each implant IMP in the second tray 182, or may create one coordinatesObject for the loose parts PRTS. The robot controller 134 may position the robot 104/vision unit 108 at the coordinates associated with each part as determined by the coordinatesObject for each part.

The inspection module 170 may also be configured to explore the system state-space (i.e., the six locomotive degrees of freedom combined with the focal depth of the liquid lens and integration time of the image sensor sensor) via policy gradient algorithms optimize control policies for locating each part. In some versions, the control policy may be defined as the state vector which maximizes the confidence score returned by the inspection module 170. For example, when a part is not located at the specified location in the kit inspection recipe 126, the inspection module 170 may instruct the robot 104 to explore the state-space using the policy gradient algorithms to locate the part within the tray while maximizing the confidence score. The learning module 171 may cooperate with the inspection module 170 to improve optimized identification and handling of such scenarios.

The visionTool subclass 224 may include variables such as type, region, matchPattern, and matchString. The type variable may be assigned a value associated with either the first camera unit 136, the second camera unit 138, or both camera units 136, 138. The region variable may be assigned coordinates and/or dimensions for a rectangle that dictates how large of a region should be imaged, for example. The matchPattern may be assigned an image associated with a pattern that is to be found in the image captured by the vision unit 108 to verify the presence of the part. For example, the matchPattern image may be a pattern that is to be matched in the one or more images captured by the first camera unit 136, the second camera unit 138, or both the camera units 136, 138. During inspection, if there is a match in the captured image to this stored image, this indicates that the part is present. If there is no match, then the part is determined by the inspection module 170 to be missing. Matching of the images may be determined by known pattern recognition algorithms, including deep learning-based pattern matching algorithms such as those described in U.S. Patent Application Pub. No. 2020/0005069 to Wang et al., incorporated herein by reference. The matchString variable may be assigned a particular string of characters that need to be matched in one or more images captured by the first camera unit 136, the second camera unit 138, or both the camera units 136, 138 to determine if the part is present. During inspection, the one or more images captured may be processed using optical character recognition (OCR), including deep learning-based OCR, to determine the characters or strings of characters present in the one or more images. These characters or strings of characters can then be compared to the matchString variable to see if there is a match. If the characters match, then the part is determined to be present. In some versions, the first camera unit 136 is used to capture images for parts that are identified via matching patterns and the second camera unit 138 is used to capture images for parts that are identified via matching strings. The inspection module 170 may use the visionTool subclass 224 to create a visionToolsObject for each part of a tray.

The opticalSettings subclass 228 may include one or more variables for adjusting a setting of one or both of the first camera unit 136 and/or the second camera unit 138 including a strobe/flash length, an exposure length, and a focal power adjustment. The strobe/flash variable determines the duration of the flash or strobe. The exposure length (i.e., shutter speed) determines a duration that an image sensor inside the camera unit is exposed (i.e., open) to light. The focal power adjustment variables determine the focal length (i.e., the distance between an optical center of a lens and the image sensor when the subject is in focus).

The above-mentioned classes and subclasses are shown in an example overall kit inspection recipe class schema 236. These classes and subclasses are instantiated to create corresponding objects for each kit inspection recipe 126. For simplicity of illustration purposes, the overall class schema 236 does not show multiple trays or multiple parts per tray; however, it is contemplated that the kit inspection recipe 126 may contain any number of trayRecipe objects and any number of partRecipe objects. Once the kit inspection recipe 126 is created, it may be saved to the database DB and retrieved at a later time for inspection of the associated surgical kit.

As previously discussed, images associated with parts that were improperly identified and therefore resulted in a need for correction by the operator may be flagged and used as training images. Periodically, the inspection module 170 and/or the learning module 171 may use the training images to optimize processes, such as to update the kit inspection recipes, update search policies for specific parts, and the like. The inspection module 170 may update any portion of the kit inspection recipes such as any value for any variable associated with the partRecipeObject, the visionToolObject, theCoordinatesObject, opticalSettingObject, the kitRecipeObject and/or the trayRecipeObject. In some versions, the inspection module 170 may update the opticalSettingObject to refine the focal length variable of the opticalSettingObject based on the training images. In some versions, the inspection module 170 may update one or more of the variables of the coordinate object to refine the position in which the robot controller 134 positions the robot 104/vision unit 108 when inspecting a particular part.

Once the kit inspection recipe 126 has been updated, the kit inspection recipe 126 may be tested. When the number of tests exceeds a certain threshold, an operator can review the inspection history of the robot 104 and determine whether or not performance was improved when compared to the performance of a prior inspection recipe. In reviewing performance, the operator van evaluate whether the rate at which parts were correctly identified improves compared to the prior inspection recipe. When the operator deems that the kit inspection recipe 126 is producing satisfactory results and performance has improved when compared to the prior kit inspection recipe, the operator may confirm that the kit inspection recipe 126 is ready for use. In the event that an update to the kit inspection recipe 126 leads to a less desirable outcome, the inspection module may restore the previous kit inspection recipe or restore a default kit inspection recipe.

Figure 8B:
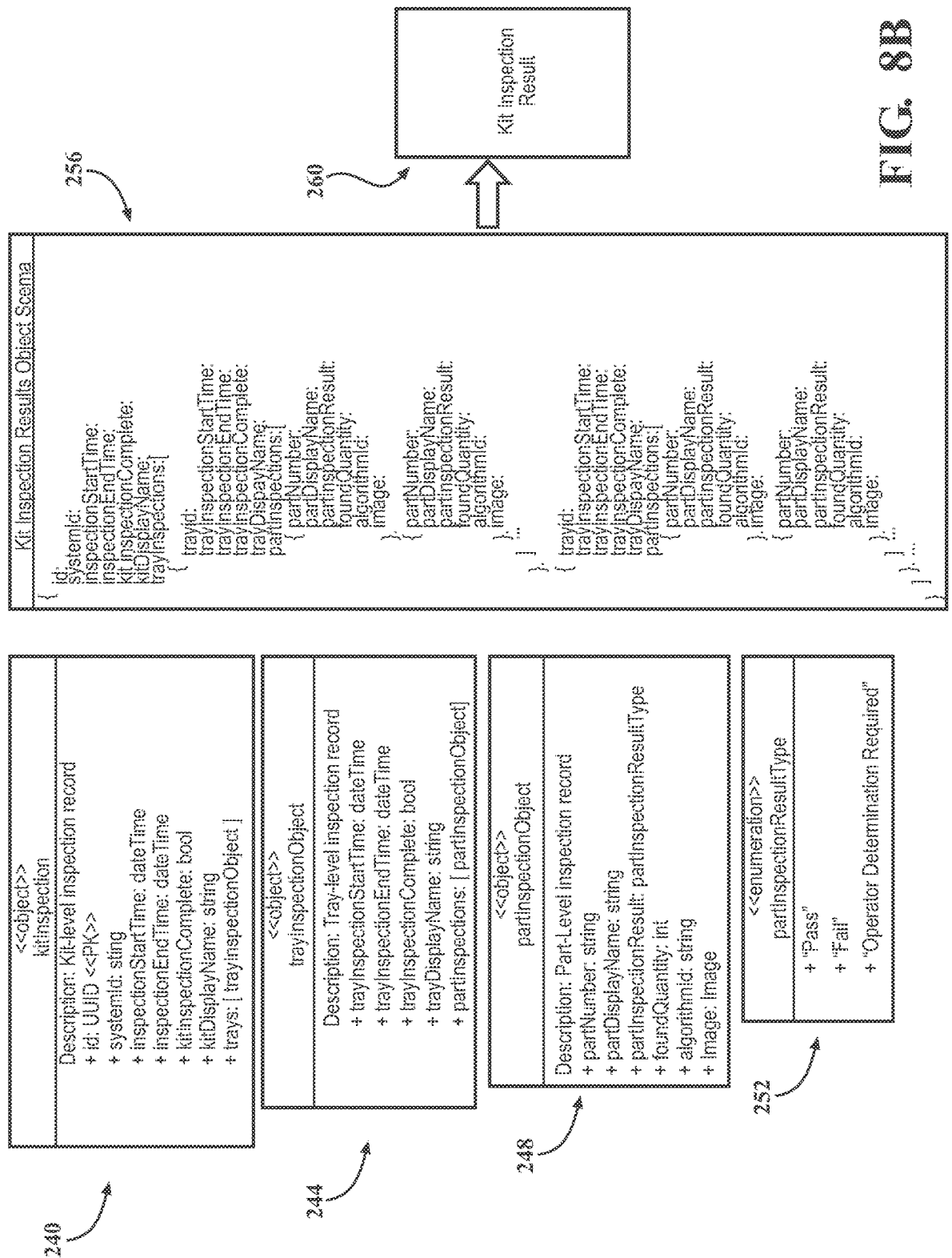
FIG. 8B is a block diagram of a kitInspection class used to create a kit inspection results object for a surgical kit.

Referring to FIG. 8B, the software operated by the inspection system 100 also provides inspection results for viewing and storing. The results are compiled in objects that are instances of inspection classes set forth in FIG. 8B. A kitInspection class 240 may be used to create a kit inspection result 260 (i.e., kit inspection results object). The kitInspection class 240 may include variables such as id, systemid, inspectionStartTime, inspectionEndTime, kitInspectionComplete, and kitDisplayName. The id variable may be assigned the unique identifier associated with the surgical kit. The systemId variable may be assigned a name or a unique identifier associated with the inspection system 100 used to inspect the surgical kit. The inspectionStartTime variable may be assigned a time corresponding to the time that the robot 104 and/or the vision unit 108 began inspection of the first part, the time that a kitInspection object was created, or the like. The inspectionEndTime may be assigned a time corresponding to when the robot 104 and/or the vision unit 108 finished inspection of the last part, the time the robot 104 was set to idle after the last tray was inspected, the time the inspection results were submitted to the inspection module 170, or the like. The kitInspectionComplete may be assigned a Boolean value, for example, true or false, with true indicating that the robot 104 and/or the vision unit 108 finished inspecting the surgical kit and false indicating that the robot 104 and/or vision unit 108 did not finish inspecting the surgical kit.

The kitInspection class 240 may also include a trayInspection subclass 244. The trayInspection subclass 244 may be used to create a trayInspectionObject for each tray in the surgical kit, for example, a trayInspectionObject for the first tray 180, a trayInspectionObject for the second tray 182, and a trayInspectionObject for the loose parts PRTS. The trayInspection subclass 244 may include one or more variables such as trayInspectionStartTime, trayInspectionEndTime, trayInspectionComplete, and trayDisplayName.

The trayInspectionStartTime variable may be assigned a time corresponding to when the robot 104 and/or the vision unit 108 started inspection of the first part in the tray. The trayInspectionEndTime variable may be assigned a time corresponding to when the robot 104 and/or the vision unit 108 finished inspection of the last part in the tray. The trayInspectionComplete variable may be assigned a Boolean value with true indicating that the robot 104 and/or the vision unit 108 finished inspecting the tray and false indicating that the robot 104 and/or the vision unit 108 did not finish inspecting the tray.

The trayInspection subclass 244 may also include a partInspection subclass 248. The partInspection subclass 248 may be used to create a partInspectionObject for each part of the tray. The partInspection subclass 248 may include one or more variables such as partNumber, partDisplayName, partInspectionResult, foundQuantity, algorithmId, and image. The partNumber variable, as previously discussed, may be assigned an existing part number of a part (e.g., serial number, etc.). The partDisplayName variable may be assigned a name of a part to be displayed for the part on the GUI of the inspection module 170. The partInspectionResult may be assigned a partInspectionResultType as shown in 252. The partInspectionResultType may include one or more predetermined values such as "Pass", "Fail", or "Operator Determination Required." The foundQuantity variable may include a number of parts found that have the same partNumber. In some cases, the foundQuantity may be either "1" (part present) or "0" (part missing). The partInspectionResultType may also include a confidence score associated with "Pass" and "Fail" which represents the degree of confidence that the correct result was returned. The algorithmId variable may correspond to a type of algorithm (identification method) used to process the one or more images captured by the first camera unit 136 and/or the second camera unit 138 for that part to determine if the part is present or missing (e.g., pattern recognition, OCR, etc.). The image variable may be assigned an image captured of the part.

The above-mentioned classes are shown in an example overall kitInspection Results class schema 256. These classes and subclasses are instantiated to create corresponding objects for each kit inspection result 260. For illustration purposes, the overall kitInspection Results class schema 256 does not show classes for multiple trays or multiple parts per tray; however, it is contemplated that the kit inspection results 260 may contain any number of trayInspectionObjects and any number of partInspectionObjects. Once the kit inspection result 260 is completed, it may be saved to the database DB and retrieved by the inspection module 170 at a later time. The kit inspection result 260 may be retrieved to determine how to replenish the surgical kit, for billing purposes, etc. The kit inspection result 260 may also be retrieved in order to determine if any adjustments need to be made to the kit inspection recipes 126 to increase a rate at which the inspection system 100 is correctly identifying parts. The kit inspection result 260 may also include a confidence score for each part, representing the degree of confidence in the inspection system correctly identifying each of the surgical parts.

Figure 8C:
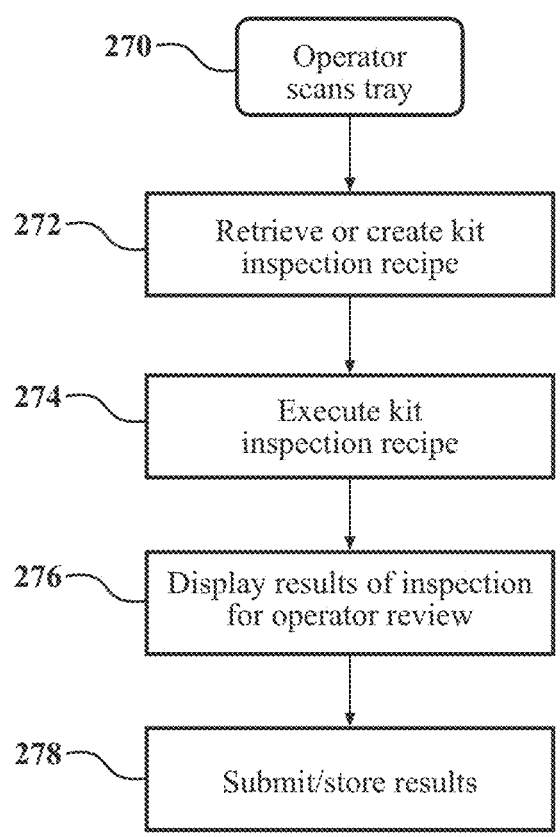
FIG. 8C is a block diagram of steps carried out in an example method performed by the inspection system.

FIG. 8C shows a high-level block diagram of steps carried out by the inspection system 100. At 270, the operator initially scans in one or more trays of a surgical kit using the reader device 176. The system controller 166 then determines the id of the surgical kit based on the scan. At 272, the system controller 166 then determines if a kit inspection recipe 126 exists by scanning the database DB storing the kit inspection recipes to see if any are associated with the id of the surgical kit. If a kit inspection recipe 126 exists that is associated with the id, the system controller 166 retrieves the associated kit inspection recipe 126 from the database DB. If there is no associated kit inspection recipe 126, the operator is prompted to find the kit inspection recipe 126 from a list of kit inspection recipes or to create a new kit inspection recipe using the classes/objects previously described with respect to FIG. 8A. Once the kit inspection recipe 126 is retrieved or created, then the robot 104 and the vision unit 108 are activated to execute the kit inspection recipe 126 at 274. The results of the kit inspection are displayed to the operator at 276 and then submitted to one or more locations at 278, e.g., stored in the database DB, submitted to a replenishing system, billing system, etc.

With reference to FIGS. 9-14, an example method 300 of using the inspection system 100 is shown. As will be appreciated from the subsequent description below, this method 300 merely represents an example and non-limiting sequence of blocks to describe operation of one or more of the controllers 134, 156, 158, 162, 166 in executing instructions from the inspection module 170 and is in no way intended to serve as a complete functional block diagram of the control system.

The method 300 may begin at 302, where the system controller 166 receives a scanned tray barcode from the reader device 176 and parses a set-type from the scanned tray barcode to determine the id (also referred to as Set-ID) of the surgical kit. At 304, the system controller 166 queries the database DB storing the kit inspection recipes 126 based on the id of the surgical kit. At 306, the system controller 166 determines whether a kit inspection recipe 126 was found. If so, the method 300 continues at 308; otherwise, the method 300 continues at A of FIG. 10.

Figure 9:
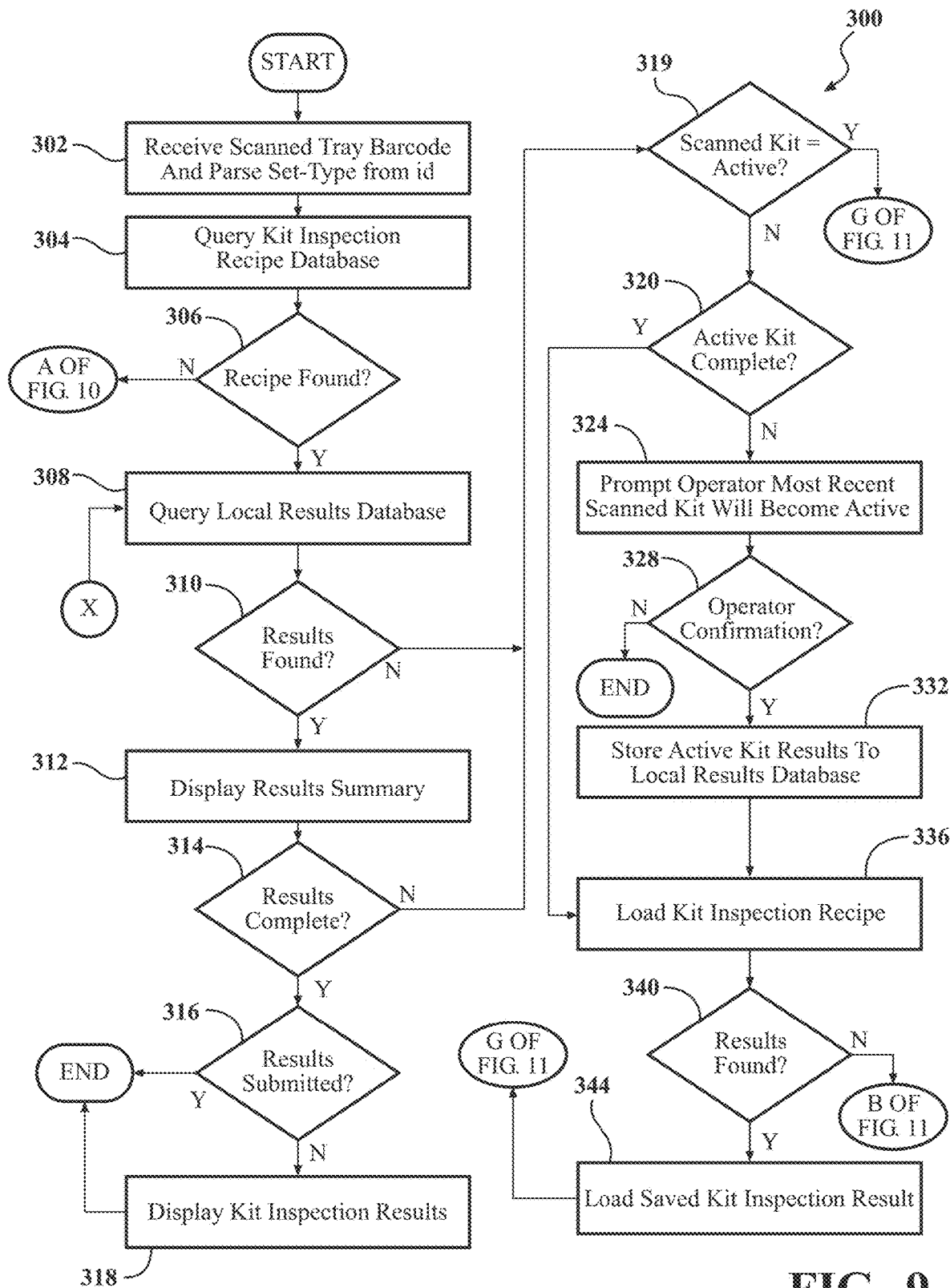
FIGS. 9-14 together form a flowchart of an example method performed by the inspection system.
Figure 10:
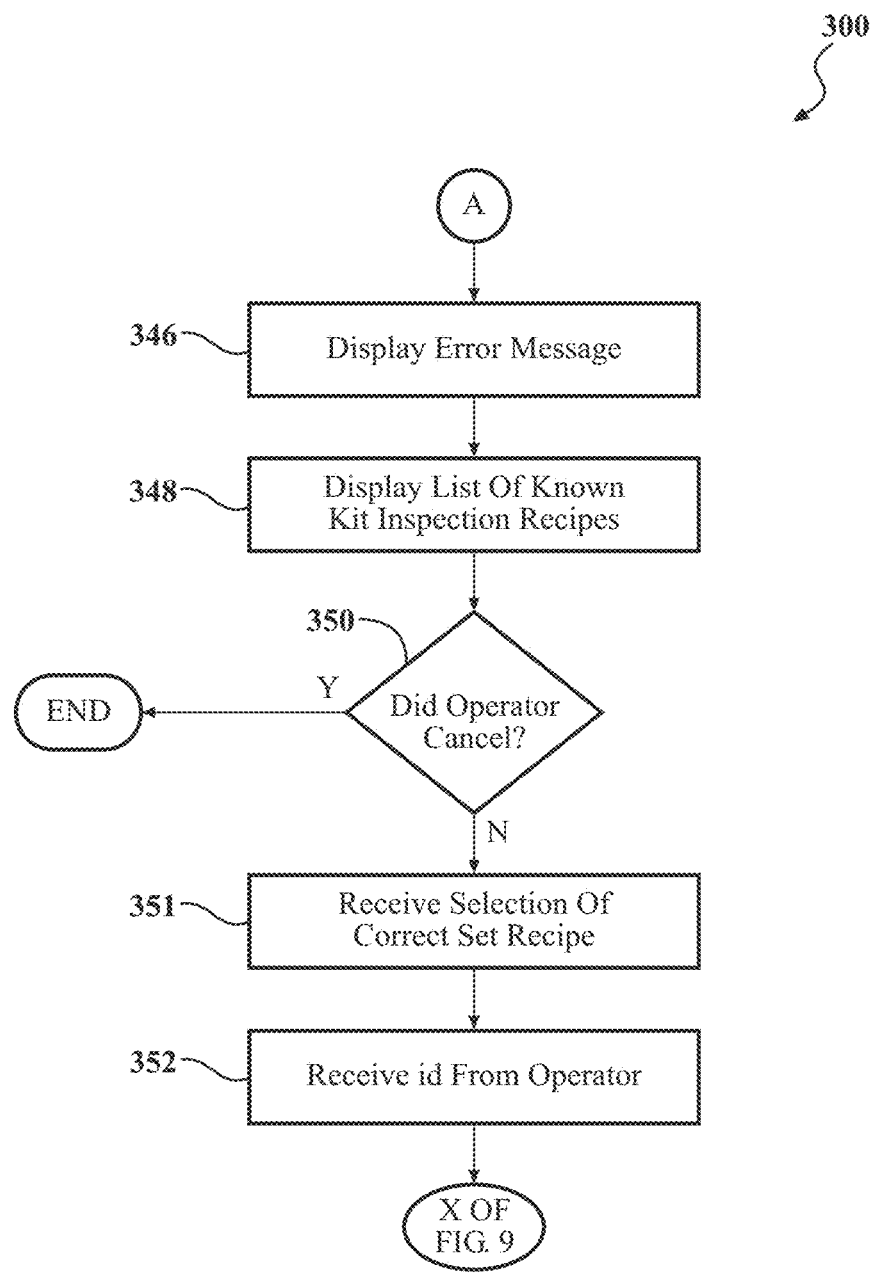

At 346 of FIG. 10, the system controller 166 displays an error message on the display 172 indicating that no kit inspection recipe 126 was found. At 348, the system controller 166 displays a list of known kit inspection recipes 126 from which the operator can manually select one of the kit inspection recipes 126. At 350, the system controller 166 determines whether the operator canceled since no kit inspection recipe 126 existed. If the operator canceled, the method 300 may end since no kit inspection recipe 126 was found and one will need to be created; otherwise, the method 300 may continue at 351. At 351, the system controller receives a selection of a correct kit inspection recipe 126 (e.g., via the user interface UI). At 352, the system controller 166 receives the id entered by the operator via the user interface UI and the method 300 continues at X of FIG. 9.

At 308 of FIG. 9, the system controller 166 queries the database DB that stores local inspection results to determine if there are already inspection results associated with the surgical kit. At 310, the system controller 166 determines whether results were found. If so, the method 300 continues at 312; otherwise, the method 300 continues at 319. At 312 the results are displayed to the operator and at 314, the system controller 166 determines whether the results are complete. If the results are complete, the method 300 continues at 316; otherwise, the method 300 continues at 319. At 316, the system controller 166 determines whether the results were submitted. If so, the method 300 may end; otherwise, the method 300 may continue at 318 where the system controller 166 displays the kit inspection results so that the operator may review the results.

At 319, the system controller 166 determines whether the scanned kit is the active kit. If so, the method 300 continues at G of FIG. 11, otherwise, the method 300 continues at 320. At 320, the system controller 166 determines whether the active kit is complete (i.e., the recently scanned kit is not yet active). If so, the method 300 may continue at 336; otherwise, the method 300 may continue at 324. At 324, the system controller 166 prompts the operator via the display 172 that the most recent scanned kit will become active. At 328, the system controller 166 determines whether operator confirmation was received. If so, the method 300 continues at 332; otherwise, the method 300 may end.

At 332, the system controller 166 stores active kit results to the database DB. At 336, the system controller 166 may load the kit inspection recipe 126 for the most recently scanned kit. At 340, the system controller 166 determines whether inspection results were found for the newly loaded kit inspection recipe. If so, the method 300 may continue at 344; otherwise, the method 300 may continue at B of FIG. 11. At 344, the system controller 166 loads the kit inspection results that were found (i.e., the saved kit inspection results object).

Figure 11:
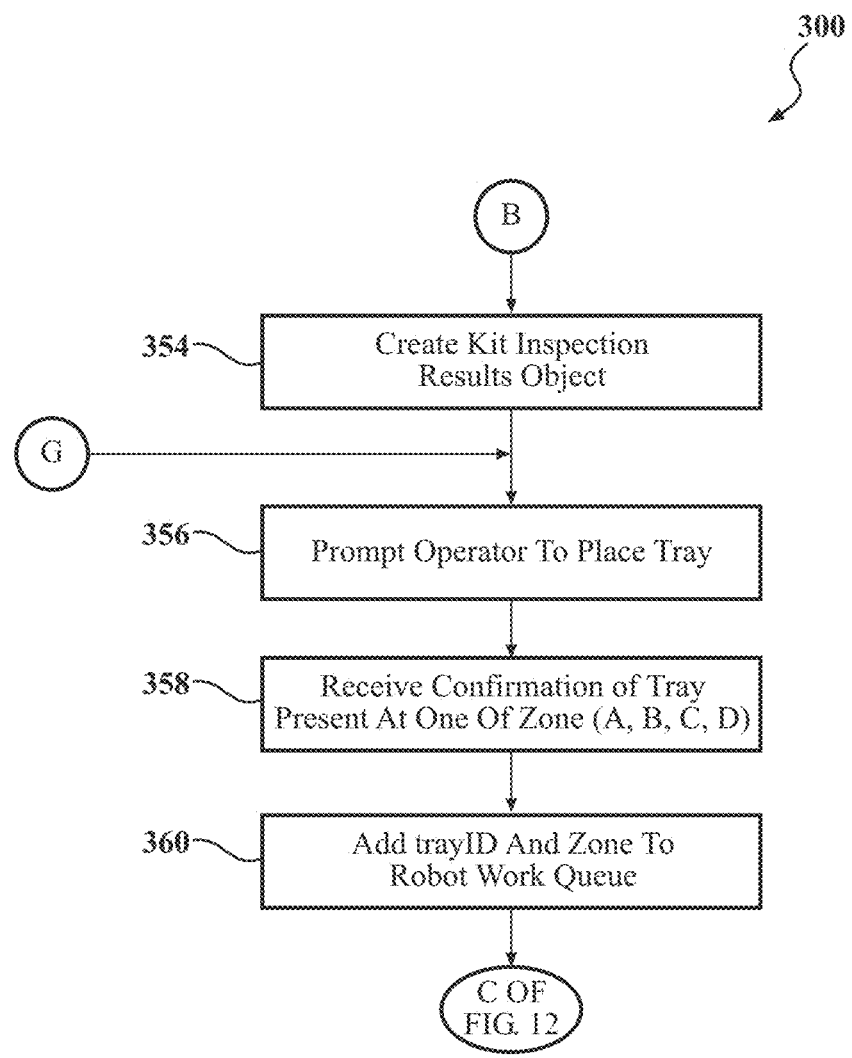

At 354 of FIG. 11, the system controller 166 creates a kit inspection results object to be ready for inspection. At 356, the system controller 166 prompts the operator via the display 172 to place a tray in one of the zones (e.g., A, B, C, or D). At 358, the system controller 166 receives confirmation of the tray being present at one of the zones (A, B, C, or D) and receives the trayId, which can be manually entered by the operator via the user interface UI or can be determined through sensing of the tray by one or more sensors at the zones (A, B, C, D) and/or by imaging the trays and identifying unique identifiers in the images (e.g., landmarks, codes, patterns, etc.). At 360, the system controller 166 adds the trayId and zone to a work queue for the robot 104 and the method 300 continues at C of FIG. 12.

Figure 12:
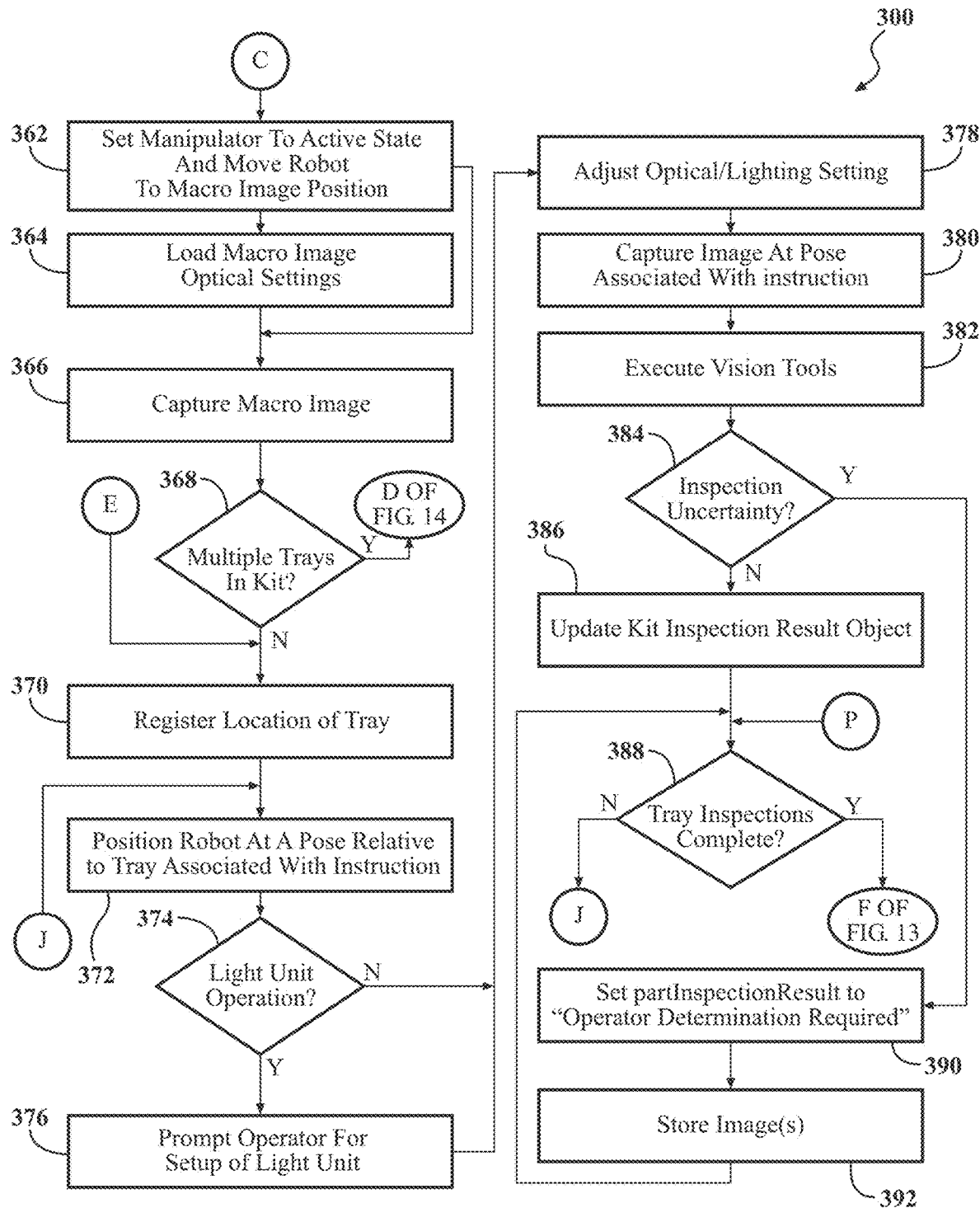
Figure 13:
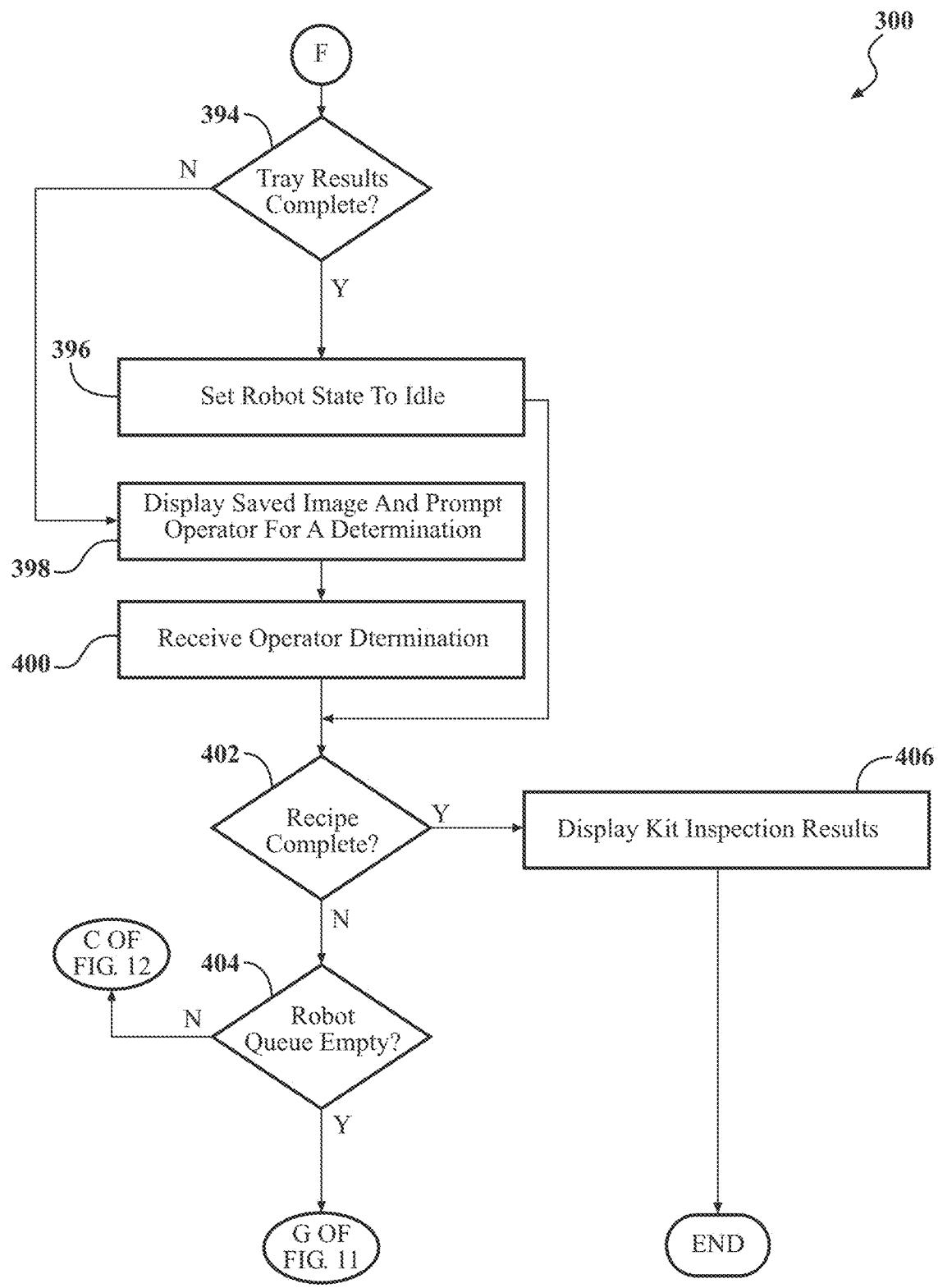

At 362 of FIG. 12, the robot controller 134 and/or the system controller 166 sets the robotic manipulator 128 to an active state and moves the robot 104 and the vision unit 108 to a macro image position configured to capture an image of the entire tray of parts. At 364, one or more of the camera controllers 156, 158 and/or the system controller 166 load macro image optical settings to ready one of the camera units 136, 138 to capture the macro image. At 366, the one of the camera units 136, 138 captures the macro image. At 368, the system controller 166 determines whether there are multiple trays in the surgical kit. If so, the method 300 continues at D of FIG. 14; otherwise, the method 300 continues at 370.

Figure 14:
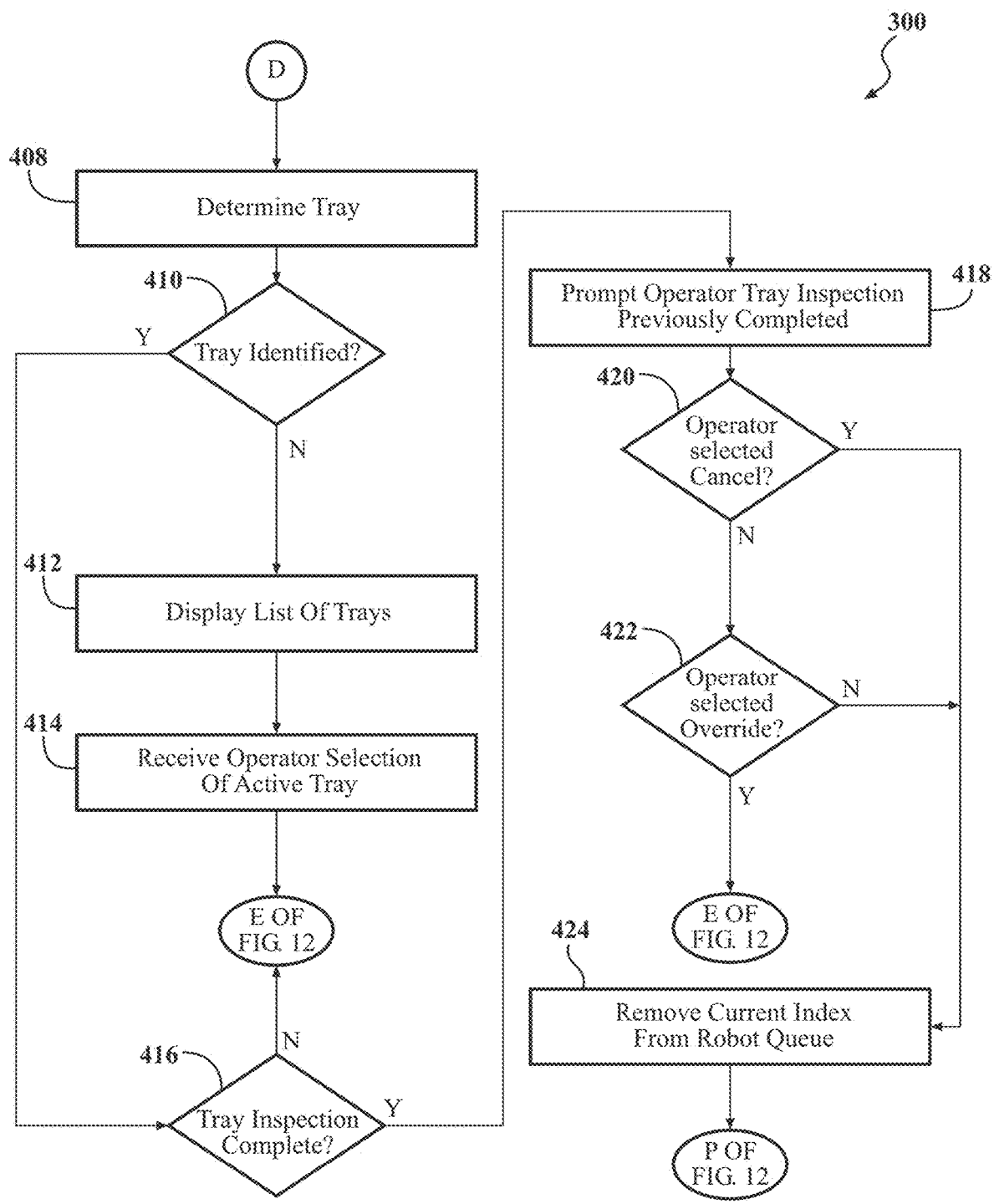

At 408 of FIG. 14, the system controller 166 determines which tray of the surgical kit the macro image is associated with. At 410, the system controller 166 determines whether the tray was identified (e.g., mansually by the operator, automatically using sensors, or automatically by imaging and identifying unique identifiers in the images, etc.). If the tray was identified, the method 300 continues at 416; otherwise, the method 300 continues at 412. At 412, the system controller 166 displays the list of trays associated with the kit inspection recipe 126 being used to inspect the surgical kit. At 414, the system controller 166 receives an operator selection of an active tray and control continues back at FIG. 12, letter E. At 416, the system controller determines whether tray inspection is complete. If so, the method 300 continues at 418; otherwise, the method 300 continues back at FIG. 12, letter E. At 418, the system controller 166 prompts a message to the operator indicating that the tray inspection was previously completed.

At 420, the system controller 166 determines whether the operator selected cancel via the user interface UI. If so, the method 300 continues at 424; otherwise, the method 300 continues at 422. At 422, the system controller 166 determines whether the operator selected override. If so, the method 300 continues back at FIG. 12, letter E; otherwise, the method 300 may continue to 424. At 424, the system controller 166 removes the current index from the work queue of the robot 104 and the method 300 continues back at FIG. 12, letter P.

At 370 of FIG. 12, the robot controller 134, camera controllers 156, 158, and/or system controller 166 registers a location of the tray. This may include determining where one or more reference features of the tray (e.g., points, lines, contours, etc.) are in the coordinate reference frame of the robot 104 and/or the coordinate reference frame of the vision unit 108. Note that the reference features used for registration may be the same features as the unique identifiers used to determine the identification of the tray. Such registration can include, for example, evaluating the macro image captured at 366 to determine a location of the one or more reference features of the tray in the coordinate reference frame of the robot 104 and/or the coordinate reference frame of the vision unit 108, and by extension, determining a pose of the tray reference frame in the coordinate reference frame of the robot 104 and/or in the coordinate reference frame of the vision unit 108. The robot controller 134, camera controllers 156, 158, and/or system controller 166 may be configured to identify the one or more reference features of the tray and their associated coordinates with respect to two or three axes (x, y, or x, y, z) to determine the tray's position and/or orientation.

In some versions, the macro image is compared to a stored image of the tray and the macro image transformed to align with the stored image using, for example, feature-based registration algorithms (e.g., finding correspondence between the reference features). By understanding the correspondence between the reference features in the images, a geometrical transformation can then be used to map the stored image and its associated tray reference frame to the macro image. In some versions, the vision unit 108 may utilize one of one or more of the following vision capabilities to determine the reference features of the tray in three dimensions: laser triangulation; stereo vision; time-of-flight; and structured light. Once registration is complete, the coordinate reference frame of the robot and/or the coordinate reference frame of the vision unit 108 can then be translated to the tray reference frame (or vice versa) since the coordinates stored in the kit inspection recipe 126 are defined with respect to the tray reference frame. By virtue of such translation, the robot controller 134 and/or the system controller 166 can now position the robotic manipulator 128 and the vision unit 108 at specific poses relative to the tray.

At 372, the robot controller 134 and/or the system controller 166 positions the robotic manipulator 128 at a pose relative to the tray in accordance with instructions from the kit inspection recipe 126 (e.g., based on the coordinates given for a part in the surgical kit). At 374, the system controller 166 determines whether the light surface unit 118 is being used. If so, the method 300 continues at 376; otherwise, the method 300 continues at 378. At 378, the camera controllers 156, 158 and/or the system controller 166 adjust optical/lighting settings based on the kit inspection recipe 126 to prepare for capturing an image. At 380, one or both of the camera units 136, 138 capture an image at a pose associated with instructions from the kit inspection recipe 126 (e.g., of a single part or of the light surface 124 if the light surface unit 118 is being used). At 382, the camera controllers 156, 158 and/or the system controller 166 execute vision tools, which include selecting the identification method being used to determine if the part (or parts) is present or missing (e.g., pattern matching, string matching (OCR), etc).

At 384, the system controller 166 determines whether there was inspection uncertainty based on, for example, a best fit analysis used in the pattern matching or string matching. If there is inspection uncertainty, the method 300 continues at 390; otherwise, the method 300 continues at 386. At 386, the system controller 166 updates the kit inspection result object with the analysis performed at 382 to determine if the part was present or missing. At 390, the system controller 166 sets the partInspectionResult variable for that part (or parts) to "Operator Determination Required." At 392, the camera controllers 156, 158 and/or the system controller 166 stores the image associated with the current part (or parts) and the method may continue to 388. At 388, the system controller 166 determines whether the tray inspections associated with the kit inspection recipe 126 are complete, i.e., has the last part of the kit inspection recipe 126 been inspected or not. If so, the method 300 may continue at letter F of FIG. 13; otherwise, the method 300 continues back at J of the current figure to inspect the next part in the predefined sequence established by the kit inspection recipe 126.

At 394, the system controller 166 determines whether the tray results are complete, i.e., has a determination been made for each part regarding whether the part is present or missing, or are there any parts that require operator determination (see 390 in FIG. 12). If the tray results are complete, the method 300 continues at 396; otherwise, the method 300 continues at 398. At 396, the robot controller 134 and/or the system controller 166 set the robot state to idle. At 398, the system controller 166 displays one or more saved images from the incomplete tray results and prompts the operator for a determination for each of the images. At 400, the system controller 166 receives an operator determination pertaining to the incomplete result. For instance, steps 398 and 400 iterate through all images for the parts where a determination of present/missing has not yet been made until the operator has made a determination for all the parts. The operator may also make determinations regarding whether each of the parts that are present are damaged/ defective. Notably, the inspection system 100 can feed these additional results determined by the operator (and the associated images) into the inspection system 100 to enhance the deep-learning algorithms that are used to inspect the parts thereby increasing the ability of the inspection system 100 to accurately determine whether parts are present/absent, damaged/defective, etc. In other words, each time the operator views an image and determines that a part is present or absent, damaged/defective, etc., the inspection system 100 now has another data set (image) that can be added to its training to make a future determination of whether the part is present/absent, damaged, defective, etc. At 402, the system controller 166 determines whether the kit inspection recipe 126 is complete (i.e., have all parts been inspected for the surgical kit). If so, the method 300 continues at 406; otherwise, the method 300 continues at 404. At 404, the robot controller 134 and/or the system controller 166 determine whether the work queue for the robot 104 is empty. If so, the method 300 continues to letter G of FIG. 11; otherwise, the method 300 continues to letter C of FIG. 12. At 406, the system controller 166 may display the kit inspection result on the display 172, and the method 300 may end. While the example method 300 is shown as "starting" and "ending" in FIGS. 9-14 for illustrative purposes, it will be appreciated that the method 300 may instead return to 302. Furthermore, as noted above, the method 300 described above and depicted in FIGS. 9-14 is in no way intended to serve as a complete functional block diagram of the control system, and other configurations are contemplated.

The foregoing description is merely illustrative in nature and is not intended to limit the disclosure, its application, or uses. The broad teachings of the disclosure can be implemented in a variety of forms or ways. Therefore, while this disclosure includes particular examples, the true scope of the disclosure should not be so limited since other modifications will become apparent upon a study of the drawings, the specification, and the following claims. It should be understood that one or more steps within a method may be executed in different order without altering the principles of the present disclosure. Further, although each of the examples is described above as having certain features, any one or more of those features described with respect to any example of the disclosure can be implemented in and/or combined with features of any of the other examples, even if that combination is not explicitly described. In other words, the described examples are not mutually exclusive, and permutations of one or more examples with one another remain within the scope of this disclosure.

Spatial and/or functional relationships between elements (for example, between controllers, etc.) are described using various terms, including "connected," "engaged," "coupled," "next to," "on top of," "above," "below," "adjacent," and "disposed." Unless explicitly described as being "direct," when a relationship between first and second elements is described in the above disclosure, that relationship can be a direct relationship where no other intervening elements are present between the first and second elements, but can also be an indirect relationship where one or more intervening elements are present (either spatially or functionally) between the first and second elements.

As may be used herein throughout the disclosure, the phrase at least one of A, B, and C should be construed to mean a logical (A OR B OR C), using a non-exclusive logical OR, and should not be construed to mean "at least one of A, at least one of B, and at least one of C." The term subset does not necessarily require a proper subset. In other words, a first subset of a first set may be coextensive with (equal to) the first set.

In the Figures, the direction of an arrow, as indicated by the arrowhead, may generally demonstrate the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

In this application as may be used, including the definitions below, the term "controller" may be replaced with the term "circuit." The term "controller" may refer to, be part of, or include the following: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The controller may include one or more circuits, such as interface circuits. In some examples, the interface circuit(s) may implement wired or wireless (WIFI) interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

Each controller may communicate with one or more other controllers using the interface circuit(s). Although the controller may be depicted in the present disclosure as logically communicating directly with other controllers, in various configurations the controller may communicate via a communications system. The communications system includes physical and/or virtual networking equipment such as hubs, switches, routers, and gateways. In some configurations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various configurations, the functionality of the controller may be distributed among multiple controllers that are connected via the communications system. For example, multiple controllers may implement the same functionality in a distributed manner. In a further example, the functionality of the controller may be split between a server (also known as remote, or cloud) controller and a client (or, user) controller.

Some or all hardware features of a controller may be defined using a language for hardware description, such as IEEE Standard 1364-2005 (commonly called "Verilog") and IEEE Standard 10182-2008 (commonly called "VHDL"). The hardware description language may be used to manufacture and/or program a hardware circuit. In some configurations, some or all features of a controller may be defined by a language, such as IEEE 1666-2005 (commonly called "SystemC"), that encompasses both code, as described below, and hardware description.

The term code, as may be used above, may include software, firmware, and/or microcode, and may refer to programs, routines, functions, classes, data structures, and/or objects. The term shared processor circuit encompasses a single processor circuit that executes some or all code from multiple controllers. The term group processor circuit, as may be used above, encompasses a processor circuit that, in combination with additional processor circuits, executes some or all code from one or more controllers. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple controllers. The term group memory circuit, as may be used above, encompasses a memory circuit that, in combination with additional memories, stores some or all code from one or more controllers.

The term memory circuit, as may be used above, is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer application and/or programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SSENSORLINK, and Python®.

The present disclosure also comprises the following clauses, with specific features laid out in dependent clauses, that may specifically be implemented as described in greater detail with reference to the configurations and drawings above.

I. A method for inspecting a kit having parts of different types using a robot and a vision unit supported by the robot, the vision unit having a first camera unit and a second camera unit, the method comprising the steps of: scanning the kit to identify the kit and obtain unique inspection instructions for the kit to control inspection of the kit; placing the kit with parts of a first type and a second type on a working table; placing loose parts on a light surface illuminated by a light source from beneath the light surface; and activating the robot such that the robot is positioned at a plurality of poses relative to each of the kits, and in a predefined sequence, in accordance with the unique inspection instructions, wherein the first camera unit and the second camera unit move relative to each of the kits during the positioning of the robot at the plurality of poses, and wherein one or both of the first camera unit and the second camera unit operate at each of the plurality of poses to capture images at each of the plurality of poses.

II. The method of clause I, comprising applying forces and torques to the vision unit to control movement of the robot.

III. An inspection system for inspecting kits having parts of different types, the inspection system comprising: one or more camera units configured to obtain images of parts of a first type and parts of a second type; a light source; a light surface to receive loose parts from the kits, the one or more camera units being configured to capture one or more images of the loose parts while the light source illuminates the light surface from beneath the light surface; a robotic manipulator supporting the one or more camera units such that the one or more camera units are capable of being moved by the robotic manipulator relative to the kits; and one or more controllers being configured to: obtain unique inspection instructions for each of the kits to control inspection of each of the kits; operate the one or more camera units to capture images; detect parts in the images captured by the one or more camera units; compare the detected parts for each of the kits to a predefined list of parts for each of the kits; and generate output indicating inspection results for each of the surgical kits.

IV. The inspection system of clause III, wherein: the one or more camera units includes a first camera unit and a second camera unit; the first camera unit configured to obtain images including unique geometric features of the parts of the first type; and the second camera unit configured to obtain images of characters on the parts of the second type.

V. The inspection system of clause IV, wherein the one or more controllers are configured to operate the first camera unit and the second camera unit independently of each other.

What is claimed is:

1. A surgical kit inspection system for inspecting surgical kits having parts of different types, the surgical kit inspection system comprising:

a first camera having a first lens to obtain images of unique geometric features of parts of a first type; and a second camera having a second lens, different than the first lens, to obtain images of characters on parts of a second type;

a robotic manipulator supporting the first and second cameras such that the first and second cameras are capable of being moved by the robotic manipulator relative to the surgical kits; and one or more controllers being configured to:
  obtain unique inspection instructions for each of the surgical kits to control inspection of each of the surgical kits;
  position the robotic manipulator at a plurality of poses relative to each of the surgical kits in accordance with the unique inspection instructions;
  operate one or both of the first camera and the second camera at each of the plurality of poses to capture images at each of the plurality of poses;
  detect parts in the images captured at each of the plurality of poses using a first identification method when utilizing the first camera and using a second identification method when utilizing the second camera;
  compare the detected parts for each of the surgical kits to a predefined list of parts for each of the surgical kits; and
  generate output indicating inspection results for each of the surgical kits.

2. The surgical kit inspection system of claim 1, wherein the robotic manipulator supports the first and second cameras such that the first and second cameras are capable of being moved by the robotic manipulator relative to a plurality of trays constituting a surgical kit.

3. The surgical kit inspection system of claim 1, comprising a light surface to receive loose parts from the surgical kits, the first camera unit being configured to capture one or more images of the loose parts.

4. The surgical kit inspection system of claim 1, wherein the robotic manipulator includes a collaborative robotic arm having one or more sensors to detect forces or torques applied to at least one of the first camera, the second camera, and the robotic manipulator by the operator to control movement of the collaborative robotic arm.

5. The surgical kit inspection system of claim 1, wherein the one or more controllers are configured to employ a deep learning algorithm as at least one of the first and second identification methods used to detect the parts in the surgical kits.

6. A method for inspecting surgical kits having parts of different types using a robot, a first camera supported by the robot, and a second camera supported by the robot, the method comprising the steps of:
  obtaining unique inspection instructions for each of the surgical kits to control inspection of each of the surgical kits;
  positioning the robot at a plurality of poses relative to each of the surgical kits in accordance with the unique inspection instructions, wherein the first camera and the second camera move relative to each of the surgical kits during the positioning of the robot at the plurality of poses;
  operating one or both of the first camera and the second camera at each of the plurality of poses to capture images at each of the plurality of poses, wherein the first camera has a first lens to obtain images of unique geometric features of parts of a first type and the second camera has a second lens, different than the first lens, to obtain images of characters on parts of a second type;
  detecting parts in the images captured at each of the plurality of poses using a first identification method when utilizing the first camera and using a second identification method when utilizing the second camera;
  comparing the detected parts in each of the surgical kits to a predefined list of parts for each of the surgical kits; and
  generating output indicating inspection results for each of the surgical kits.

7. The method of claim 6, wherein positioning the robot at a plurality of poses relative to each of the surgical kits in accordance with the unique inspection instructions includes positioning the robot relative to a plurality of trays constituting a surgical kit.

8. The method of claim 6, comprising illuminating loose parts from the surgical kits on a light surface such that the first camera can capture one or more images of the loose parts.

9. The method of claim 6, comprising sensing forces and torques acting on the robot that are applied by the operator to control movement of the robot.

10. The method of claim 6, comprising processing a deep learning algorithm as at least one of the first and second identification methods used to detect the parts in the surgical kits.

11. The method of claim 6, wherein generating output indicating inspection results for each of the surgical kits includes generating output that indicates one or more of the following: if any parts are missing; if any parts are in a wrong location; or if any parts have a defect.

12. An inspection system for inspecting kits having parts of different types, the inspection system comprising:
  one or more cameras configured to obtain images of at least one of: unique geometric features of parts of a first type, and characters on parts of a second type;
  a robotic manipulator supporting the one or more cameras such that the one or more cameras are capable of being moved by the robotic manipulator relative to the kits; and
  one or more controllers being configured to:
    obtain unique inspection instructions for each of the kits to control inspection of each of the kits;
    position the robotic manipulator at a plurality of poses relative to each of the kits in accordance with the unique inspection instructions;
    operate the one or more cameras at each of the plurality of poses to capture images at each of the plurality of poses;
    detect parts in the images captured at each of the plurality of poses using at least one of a first identification method and a second identification method;
    compare the detected parts in each of the kits to a predefined list of parts for each of the kits; and
    generate output indicating inspection result for each of the kits.

13. The inspection system of claim 12, wherein the one or more cameras includes a first camera having a first imaging lens and a first liquid lens to obtain the images of unique geometric features of the parts of the first type.

14. The inspection system of claim 13, wherein the one or more controllers are configured to use the first identification method to detect the parts of the first type in the images when utilizing the first camera.

15. The inspection system of claim 13, wherein the one or more cameras includes a second camera having a second imaging lens, different than the first imaging lens, and a second liquid lens to obtain images of characters on the parts of the second type.

16. The inspection system of claim 15, wherein the robotic manipulator supports the first and second cameras such that the first and second cameras are capable of being moved by the robotic manipulator relative to a plurality of trays constituting a kit.

17. The inspection system of claim 15, wherein the one or more controllers are configured to use the second identification method to detect the parts of the second type in the images when utilizing the second camera.

18. The inspection system of claim 13, comprising a light surface to receive loose parts from the kits, the first camera being configured to capture one or more images of the loose parts.

19. The inspection system of claim 13, wherein the robotic manipulator includes a collaborative robotic arm having one or more sensors to detect forces or torques applied to the one or more cameras by the operator to control movement of the collaborative robotic arm.

20. The inspection system of claim 13, wherein the output generated by the one or more controllers indicates one or more of the following: if any parts are missing; if any parts are in a wrong location; or if any parts have a defect.

* * * * *